(12) United States Patent
Kwak et al.

(10) Patent No.: US 7,869,040 B1
(45) Date of Patent: Jan. 11, 2011

(54) MEASUREMENT SYSTEMS CONFIGURED TO PERFORM MEASUREMENTS OF A SPECIMEN AND ILLUMINATION SUBSYSTEMS CONFIGURED TO PROVIDE ILLUMINATION FOR A MEASUREMENT SYSTEM

(75) Inventors: Hidong Kwak, San Jose, CA (US); Shankar Krishnan, Santa Clara, CA (US); Shing Lee, Fremont, CA (US); Haixing Zou, Sunnyvale, CA (US)

(73) Assignee: KLA-Tencor Technologies Corp., Milpitas, CA (US)

( * ) Notice: Subject to any disclaimer, the term of this patent is extended or adjusted under 35 U.S.C. 154(b) by 126 days.

(21) Appl. No.: 12/184,419

(22) Filed: Aug. 1, 2008

Related U.S. Application Data

(62) Division of application No. 11/058,153, filed on Feb. 14, 2005, now Pat. No. 7,408,641.

(51) Int. Cl.
*G01J 4/00* (2006.01)
(52) U.S. Cl. ..................................................... 356/369
(58) Field of Classification Search ........................ None
See application file for complete search history.

(56) References Cited

U.S. PATENT DOCUMENTS

| | | | |
|---|---|---|---|
| 4,905,170 A | 2/1990 | Forouhi et al. |
| 4,999,014 A | 3/1991 | Gold et al. |
| 5,166,752 A | 11/1992 | Spanier et al. |
| 5,181,080 A | 1/1993 | Fanton et al. |
| 5,486,701 A | 1/1996 | Norton et al. |
| 5,489,980 A | 2/1996 | Anthony |
| 5,608,526 A | 3/1997 | Piwonka-Corle et al. |
| 5,747,813 A | 5/1998 | Norton et al. |
| 5,771,094 A | 6/1998 | Carter et al. |

(Continued)

FOREIGN PATENT DOCUMENTS

WO    WO 99/45340    9/1999

(Continued)

OTHER PUBLICATIONS

International Search Report, PCT/US05/16843, mailed Jan. 20, 2006.

(Continued)

*Primary Examiner*—Tu T Nguyen
(74) *Attorney, Agent, or Firm*—Ann Marie Mewherter

(57) ABSTRACT

An illumination subsystem configured to provide illumination for a measurement system includes first and second light sources configured to generate light for measurements in different wavelength regimes. The illumination subsystem also includes a TIR prism configured to be moved into and out of an optical path from the first and second light sources to the measurement system. If the TIR prism is positioned out of the optical path, light from only the first light source is directed along the optical path. If the TIR prism is positioned in the optical path, light from only the second light source is directed along the optical path. Various measurement systems are also provided. One measurement system includes an optical subsystem configured to perform measurements of a specimen using light in different wavelength regimes directed along a common optical path. The different wavelength regimes include vacuum ultraviolet, ultraviolet, visible, and near infrared wavelength regimes.

7 Claims, 20 Drawing Sheets

U.S. PATENT DOCUMENTS

| | | | |
|---|---|---|---|
| 5,818,596 | A | 10/1998 | Imai et al. |
| 5,859,702 | A | 1/1999 | Lindblom |
| 5,877,859 | A | 3/1999 | Aspnes et al. |
| 5,910,842 | A | 6/1999 | Piwonka-Corle et al. |
| 5,953,446 | A | 9/1999 | Opsal et al. |
| 6,052,401 | A | 4/2000 | Wiesser et al. |
| 6,177,995 | B1 | 1/2001 | Compain et al. |
| 6,181,421 | B1 | 1/2001 | Aspnes et al. |
| 6,184,984 | B1 | 2/2001 | Lee et al. |
| 6,211,957 | B1 | 4/2001 | Erdosan et al. |
| 6,222,199 | B1 | 4/2001 | Freeouf |
| 6,261,853 | B1 | 7/2001 | Howell et al. |
| 6,269,144 | B1 | 7/2001 | Dube et al. |
| 6,282,222 | B1 | 8/2001 | Wieser et al. |
| 6,313,466 | B1 | 11/2001 | Olsen et al. |
| 6,325,078 | B2 | 12/2001 | Kamieniecki |
| 6,400,089 | B1 | 6/2002 | Salvermoser et al. |
| 6,440,760 | B1 | 8/2002 | Cho et al. |
| 6,456,362 | B1 | 9/2002 | Banine |
| 6,483,584 | B1 * | 11/2002 | Lee et al. .................... 356/369 |
| 6,515,746 | B2 | 2/2003 | Opsal et al. |
| 6,519,045 | B2 | 2/2003 | Kwon |
| 6,522,717 | B1 | 2/2003 | Murakami et al. |
| 6,532,076 | B1 | 3/2003 | Sidorowich |
| 6,535,286 | B1 | 3/2003 | Green et al. |
| 6,555,485 | B1 | 4/2003 | Liv et al. |
| 6,559,007 | B1 | 5/2003 | Weimer |
| 6,583,876 | B2 | 6/2003 | Opsal et al. |
| 6,591,024 | B2 | 7/2003 | Westbrook |
| 6,610,614 | B2 | 8/2003 | Niimi et al. |
| 6,610,615 | B1 | 8/2003 | McFadden et al. |
| 6,611,330 | B2 | 8/2003 | Lee et al. |
| 6,624,393 | B2 | 9/2003 | Howell et al. |
| 6,633,831 | B2 | 10/2003 | Nikoonahad et al. |
| 6,710,354 | B1 | 3/2004 | Koch et al. |
| 6,714,300 | B1 | 3/2004 | Rosencwaig et al. |
| 6,723,663 | B1 | 4/2004 | Wieczorek et al. |
| 6,757,051 | B2 | 6/2004 | Takahashi et al. |
| 6,784,993 | B2 | 8/2004 | Opsal et al. |
| 6,800,852 | B2 | 10/2004 | Larson et al. |
| 6,813,026 | B2 | 11/2004 | McAnich |
| 6,870,598 | B2 | 3/2005 | Nishi |
| 6,910,842 | B1 | 6/2005 | Yeaple |
| 7,033,846 | B2 | 4/2006 | Yu |
| 7,061,614 | B2 | 6/2006 | Wang et al. |
| 7,067,818 | B2 | 6/2006 | Harrison |
| 7,067,819 | B2 | 6/2006 | Janik |
| 7,126,131 | B2 | 10/2006 | Harrison et al. |
| 7,253,901 | B2 | 8/2007 | Janik et al. |
| 7,349,079 | B2 | 3/2008 | Zhao et al. |
| 7,359,052 | B2 | 4/2008 | Fielden et al. |
| 7,369,233 | B2 | 5/2008 | Nikoonahad et al. |
| 7,394,551 | B2 | 7/2008 | Harrison et al. |
| 7,408,641 | B1 | 8/2008 | Kwak et al. |
| 2002/0018217 | A1 | 2/2002 | Weber-Grabau et al. |
| 2002/0188417 | A1 * | 12/2002 | Levy et al. ................. 702/155 |
| 2003/0047692 | A1 | 3/2003 | Nagasaka et al. |
| 2003/0073255 | A1 | 4/2003 | Narayanan |
| 2003/0179985 | A1 | 9/2003 | Zhou |
| 2004/0196549 | A1 | 10/2004 | Aono |
| 2005/0252752 | A1 | 11/2005 | Fielden et al. |
| 2006/0182329 | A1 | 8/2006 | Yamada et al. |
| 2008/0252889 | A1 | 10/2008 | Fielden et al. |

FOREIGN PATENT DOCUMENTS

| | | |
|---|---|---|
| WO | WO 00/65331 | 11/2000 |
| WO | WO 02/25723 | 3/2002 |

OTHER PUBLICATIONS

Boher et al. "Precise Characterization of Resists and Thin Gate Dielectrics in The VUV Range OFR 157 nm Lithography," Mat. Res. Soc. vol. 636 (2001).

Boher et al., "A New Purged UV Spectroscopic Ellipsometer to Characterize Thin Film and Multilayers at 157 nm," SPIE vol. 3998 (2000).

European Search Report for European Appln. No. 05751944.9 dated Apr. 11, 2008.

Gulliksen, E. et al. "A Soft X-ray/EUV Reflectometer Based on a Laser Produced Plasma Source." Journal of X-ray Science and Technology 3, (1992), pp. 283-299.

Herman, P.R. et al. "F2-lasers: high resolution micromachining system for shaping photonic complenents" Conference on Lasers & Electro-optics. (CLEO 2001). Technical Digest Post Conference Edition. Baltimore, MD, May 6-11, 2001, Trends in Optics & Photonics (Tops), US, Washington, WA: OSA, US, vol. 56, May 6, 2001, pp. 574-575.

OBB Light Sources—Lamp Emission Spectra. Datasheet [online]. Photon Technology International, 2004; http://www.pti-nj.com/obb_spectra.html.

Mount et al. "Comprehensive analysis of gratings for ultraviolet space instrumentation," Applied Optics. vol. 17, No. 19, Oct. 1978, pp. 3108-3116.

Mount et al. "Compact far ultraviolet emission source with rich spectral emission 1150-3100 A," Applied Optics, vol. 16, No. 3, Mar. 1977, pp. 591-595.

Samson et al., "Vaccum Ultraviolet Spectroscopy I" Academic Press 1998, p. 77.

Synowicki, R.A. et al. "Optical properties of bulk c-ZrO2, c-MgO and a-As2S3 determined by variable angle spectroscopic ellipsometry" Preparation & Characterization, Elsevier Sequoia, NL, vol. 455-456, May 1, 2004, pp. 248-255.

Tiwald et al. "Measurement of Rutile TiO2 Dielectric Tensor from 0.148 to 33 um Using generalized Ellipsometry." SPIE vol. 4103 (2000).

U.S. Appl. No. 60/974,030 (Bhaskar et al.) entitled Systems and Methods for Creating Persistant Data for a Wafer and for Using Persistant Data for Inspection-Related Functions filed on Sep. 20, 2007.

VUV-VASE Variable Angle Spectroscopic Ellispometer from Vacuum Ultraviolet to Near Infrared Flyer, J.A. Woollam Co., Inc. (2003).

Wagner et al. "Materials Characterization in the Vacuum Ultraviolet with Variable Angle Spectroscopic Ellipsometry" Phys. Stat. Sol. (a) 188, No. 4, (2001).

S. Wang et al., "ARCES: an echelle spectrograph for the Astrophysical Research Consortium (ARC) 3.5m telescope," SPIE Proc. 4841, 1145-1156 (2003).

* cited by examiner $$\delta(\lambda) = \theta_{i1} - \alpha + \arcsin(\sin \alpha \sqrt{n(\lambda)^2 - \sin^2 \theta_{i1}} - \cos \alpha \sin \theta_{i1})$$

OPTIMAL WORKING RANGE FOR THE MOST COMMONLY REQUESTED GRATINGS

| Blaze | 50 g/mm | 75 g/mm | 150 g/mm | 300 g/mm | 600 g/mm | 1200 g/mm | 1800 g/mm | 2400 g/mm | 3600 g/mm |
|---|---|---|---|---|---|---|---|---|---|
| 250 nm | | | | | | | 190-450 nm | 190-450 nm | 190-450 nm |
| 300 nm | | | 200-500 nm | 200-500 nm | 200-500 nm | 200-500 nm | | | |
| 500 nm | | | 330-950 nm | 330-900 nm | 330-900 nm | 330-900 nm | 330-850 nm | | |
| 600 nm | 400-1200 nm | | | | | | | | |
| 750 nm | | | | | | 500-1400 nm | | | |
| 800 nm | | | 475-1300 nm | | | | | | |
| 1 μm | | | | 650-1800 nm | 650-1800 nm | | | | |
| 1.6 μm | | | | | 1 - 2.4 μm | | | | |
| 2 μm | | | | 1.3 - 3 μm | | | | | |
| 4 μm | | | 2.6-6 μm | | | | | | |
| 8 μm | | 5-13 μm | | | | | | | |
| Holographic | | | | | | 190-400 nm; 450-1400 nm | | 190-450 nm; 400-700 nm | 190-450 nm |

FIG. 21

MEASUREMENT SYSTEMS CONFIGURED TO PERFORM MEASUREMENTS OF A SPECIMEN AND ILLUMINATION SUBSYSTEMS CONFIGURED TO PROVIDE ILLUMINATION FOR A MEASUREMENT SYSTEM

PRIORITY CLAIM

This application is a divisional of U.S. patent application Ser. No. 11/058,153 entitled "Measurement Systems Configured to Perform Measurements of a Specimen and Illumination Subsystems Configured to Provide Illumination for a Measurement System," filed Feb. 14, 2005, issued as U.S. Pat. No. 7,408,641 on Aug. 5, 2008 to Kwak et al., which is incorporated by reference as if fully set forth herein.

BACKGROUND OF THE INVENTION

1. Field of the Invention

The present invention generally relates to measurement systems configured to perform measurements of a specimen and illumination subsystems configured to provide illumination for a measurement system. Certain embodiments relate to a measurement system in which VUV and non-VUV light is directed along a common optical path.

2. Description of the Related Art

The following description and examples are not admitted to be prior art by virtue of their inclusion in this section.

Optical systems play a significant role in the manufacturing of integrated circuits and other semiconductor devices. For example, optical metrology and/or inspection tools are used for quality control purposes in semiconductor manufacturing. The capability and throughput of these optical systems can have a significant impact on semiconductor manufacturing. For example, the throughput of an optical metrology and/or inspection tool has a direct impact on the throughput of a semiconductor manufacturing process (e.g., as the throughput of the tool decreases, the throughput of the process decreases). Likewise, the resolution capability of an optical metrology and/or inspection tool can have a significant impact on a semiconductor manufacturing process since the accuracy of the optical metrology and/or inspection tool can directly affect how well the process is controlled.

The resolution of an optical system depends to a large extent on the wavelength of the optical system as well as other parameters such as numerical aperture (NA). For example, as the wavelength of the optical system is decreased, the optical system can image features having smaller and smaller dimensions thereby increasing the resolution of the system. Some metrology and/or inspection tools used in semiconductor manufacturing today are designed for use with light having a wavelength of 248 nm. However, metrology and/or inspection tools that are designed for use with light having a wavelength of 193 nm or shorter (for example, 157 nm) are becoming more common in semiconductor research and manufacturing.

Metrology and/or inspection tools may be designed for such wavelengths since lithography tools are also designed for these wavelengths. For example, such wavelengths are sometimes used to examine materials such as resists at the wavelengths to which they will be exposed during a lithography process. In addition, a great deal of information about these wavelengths of light and the issues surrounding their implementation in optical tools is generated during the lithography tool design process that can be used to aid in the design of a metrology and/or inspection tool. Optical metrology and/or inspection tools that operate at vacuum ultraviolet (VUV) wavelengths are also being developed for semiconductor research and manufacturing as these wavelengths of light will be used in future lithography processes.

Spectroscopic measurements are also becoming more and more important in many areas, especially in semiconductor industries. To meet the next generation tool requirements, measurements across a broader spectral range must be provided. It is greatly desirable to use a spectrum that is as broad as possible with a single light source. However, it is difficult to find a single light source covering a broad enough spectrum, for example, from VUV to infrared (IR). Most of the time, it is necessary to use several light sources to cover the required broadband spectrum.

Several different ways of coupling different light sources into a common optical path are currently being used. For example, one previous approach is to use a "see-thru" lamp. This technique combines a deuterium lamp with a tungsten lamp. One of the lamps is imaged into the other lamp which has a see-thru configuration. This technique only applies to see-thru lamps and adds complexity to the optical subsystem in that additional imaging optics are required.

Another technique for combining light beams from different light sources is to use a flip-in mirror. However, a flip-in mirror will create residual polarization in the deflected beam. As such, this technique cannot be used in some forms of ellipsometry or reflectometry applications because the residual polarization due to the reflection on the flip-in mirror will distort the measurements. It is possible to correct the residual polarization effect; however, such corrections require additional calibration procedures and degrade the accuracy of the measurement system.

A different technique for increasing the spectroscopic capability of a measurement system is to use two or more separate optical subsystems combined into one measurement system. However, combining separate optical subsystems into a measurement system greatly increases the cost of the measurement system. In addition, multiple optical subsystems require additional calibrations and increase the complexity of the measurement system.

Two different measurement systems, each configured to perform measurements in different wavelength regimes, may also be used to measure a specimen such that measurements across a much broader range of wavelengths may be achieved. However, using a combination of measurement systems increases the cost of hardware and software. In addition, the use of a combination of measurements from different systems to obtain information on one specimen makes the calibration and matching of the different systems complex and difficult.

Accordingly, it would be advantageous to develop illumination subsystems that can provide illumination for a measurement system across a relatively wide range of wavelengths (e.g., from VUV to IR) without introducing residual polarization to the light, without substantially increasing the complexity or cost of the measurement system, and without requiring additional calibrations while maintaining the accuracy of the measurement system.

SUMMARY OF THE INVENTION

An embodiment of the invention relates to an illumination subsystem configured to provide illumination for a measurement system. The illumination subsystem includes a first light source and a second light source configured to generate light for measurements in different wavelength regimes. The illumination subsystem also includes a total internal reflection (TIR) prism configured to be moved into and out of an optical path from the first and second light sources to the measurement system. If the TIR prism is positioned out of the optical path, light from only the first light source is directed along the optical path to the measurement system. If the TIR prism is positioned in the optical path, light from only the second light source is directed along the optical path to the measurement system.

In one embodiment, the first light source is a xenon arc lamp. In another embodiment, the second light source is a deuterium lamp. In an additional embodiment, the first or second light source is configured to generate vacuum ultraviolet (VUV) light for the measurements. In a further embodiment, the first or second light source is configured to generate ultraviolet (UV) light, visible light, near infrared (NIR) light, or a combination thereof. The different wavelength regimes in combination may span a range of wavelengths from a VUV wavelength to an NIR wavelength.

In an embodiment, the measurement system may be configured to perform spectroscopic measurements. In another embodiment, the measurement system is configured to perform spectroscopic ellipsometry (SE) measurements. In a further embodiment, the measurement system may be configured to perform broadband spectroscopic ellipsometry (BBSE) measurements. In an additional embodiment, the measurement system is configured to perform rotating polarizer spectroscopic ellipsometry (RPSE) measurements. In a different embodiment, the measurement system is configured to perform spectroscopic reflectometry measurements.

In some embodiments, the TIR prism may be a 45 degree fused silica prism. The TIR prism preferably introduces substantially no residual polarization to the light from the second light source. In another embodiment, the illumination subsystem may include an additional TIR prism configured to direct the light from the first light source along the optical path. In one such embodiment, the additional TIR prism introduces substantially no residual polarization to the light from the first light source. The additional TIR prism may allow for a reduction in a size of the illumination subsystem. Each of the embodiments of the illumination subsystem and the measurement system described above may be further configured as described herein.

Another embodiment relates to a measurement system configured to perform measurements of a specimen. The measurement system includes a first measurement subsystem configured to perform measurements of the specimen along an optical path in a first direction. The measurement system also includes a second measurement subsystem configured to perform measurements of the specimen along the optical path in a second direction that is opposite to the first direction. Optical components positioned in the optical path are used by the first and second measurement subsystems for the measurements.

In one embodiment, the measurements of the first and second measurement subsystems include SE measurements. In another embodiment, the measurements of the first and second measurement subsystems are performed at different wavelengths. For example, the first measurement subsystem may be configured to perform the measurements at UV wavelengths, visible wavelengths, NIR wavelengths, or a combination thereof, and the second measurement system may be configured to perform the measurements at VUV wavelengths.

In an embodiment, the first measurement subsystem may be configured as an RPSE, and the second measurement subsystem may be configured as a rotating analyzer spectroscopic ellipsometer (RASE). In a different embodiment, the first and second measurement subsystems may be configured as rotating compensator spectroscopic ellipsometers (RCSE). Each of the embodiments of the measurement system described above may be further configured as described herein.

An additional embodiment relates to a different measurement system configured to perform measurements of a specimen. This measurement system includes an optical subsystem configured to perform the measurements of the specimen using light in different wavelength regimes directed along a common optical path. The different wavelength regimes include VUV, UV, visible, and NIR wavelength regimes.

In one embodiment, the optical subsystem may include a broadband light source. In another embodiment, the optical subsystem may include two or more light sources. Each of the two or more light sources may be configured to produce the light for the measurements in at least one of the different wavelength regimes.

In some embodiments, the optical subsystem may include a spectrometer that is configured to detect the light in the different wavelength regimes. The spectrometer may include a prism dispersion element and one or more order blocking filters. In one such embodiment, the spectrometer may also include a detection element. The one or more order blocking filters may be configured to allow two or more grating orders to impinge on the detection element. Each of the two or more grating orders is used for the measurements in different wavelength ranges across the different wavelength regimes. In a different embodiment, the optical subsystem may include a TIR prism configured to direct at least two of the different wavelength regimes to different detection elements.

In another embodiment, the measurement system may include a measurement chamber in which the optical subsystem is disposed. The measurement chamber is coupled to a recycle loop. The recycle loop is configured to purify a purge gas from a purge gas source or the measurement chamber and to supply the purified purge gas to the measurement chamber. In one embodiment, the measurement system is configured as a single BBSE. Each of the embodiments of the measurement system described above may be further configured as described herein.

BRIEF DESCRIPTION OF THE DRAWINGS

Further advantages of the present invention may become apparent to those skilled in the art with the benefit of the following detailed description of the preferred embodiments and upon reference to the accompanying drawings in which:

FIG. 21 is a chart illustrating the working wavelength ranges for commonly used gratings;

Figure 1:
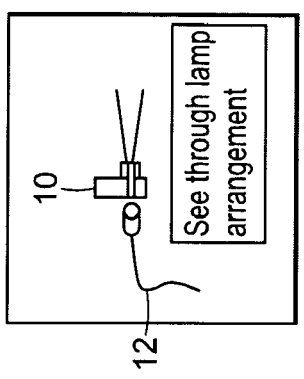
FIG. 1 is a schematic diagram illustrating a side view of a "see-thru" lamp configuration that can be used to combine light beams from multiple light sources.

While the invention is susceptible to various modifications and alternative forms, specific embodiments thereof are shown by way of example in the drawings and may herein be described in detail. The drawings may not be to scale. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

As used herein, the term "specimen" generally refers to a wafer or a reticle. As used herein, the term "wafer" generally refers to substrates formed of a semiconductor or non-semiconductor material. Examples of such a semiconductor or non-semiconductor material include, but are not limited to, monocrystalline silicon, gallium arsenide, and indium phosphide. Such substrates may be commonly found and/or processed in semiconductor fabrication facilities.

A wafer may include only the substrate such as a virgin wafer. Alternatively, a wafer may include one or more layers formed upon a substrate. For example, such layers may include, but are not limited to, a resist, a dielectric material, and a conductive material. A resist may include any material that may be patterned by an optical lithography technique, an e-beam lithography technique, or an X-ray lithography technique. Examples of a dielectric material include, but are not limited to, silicon dioxide, silicon nitride, silicon oxynitride, and titanium nitride. Additional examples of a dielectric material include "low-k" dielectric materials such as Black Diamond™ which is commercially available from Applied Materials, Inc., Santa Clara, Calif., and CORAL™ commercially available from Novellus Systems, Inc., San Jose, Calif., "ultra-low k" dielectric materials such as "xerogels," and "high-k" dielectric materials such as tantalum pentoxide. In addition, examples of a conductive material include, but are not limited to, aluminum, polysilicon, and copper.

One or more layers formed on a wafer may be patterned or unpatterned. For example, a wafer may include a plurality of dies having repeatable pattern features. Formation and processing of such layers of material may ultimately result in completed semiconductor devices. As such, a wafer may include a substrate on which not all layers of a complete semiconductor device have been formed or a substrate on which all layers of a complete semiconductor device have been formed. The term "semiconductor device" is used interchangeably herein with the term "integrated circuit."

The specimen may further include at least a portion of a thin-film head die formed on a wafer, at least a portion of a micro-electro-mechanical system (MEMS) device formed on a wafer, flat panel displays, magnetic heads, magnetic and optical storage media, and at least a portion of other components that may include photonics and optoelectronic devices such as lasers, waveguides and other passive components processed on wafers, print heads, and bio-chip devices processed on wafers.

A "reticle" or a "mask" is generally defined as a substantially transparent substrate having substantially opaque regions formed thereon and configured in a pattern. The substrate may include, for example, a glass material such as quartz. A reticle may be disposed above a resist-covered wafer during an exposure step of a lithography process such that the pattern on the reticle may be transferred to the resist. For example, substantially opaque regions of the reticle may protect underlying regions of the resist from exposure to an energy source. Many different types of reticles are known in the art, and the term "reticle" as used herein is intended to encompass all known types of reticles.

As used herein, the term "vacuum ultraviolet light" or "VUV light" refers to ultraviolet light that will be significantly absorbed by air, oxygen, carbon dioxide, and water molecules. VUV light generally includes light having a wavelength of less than about 190 nm. The term "non-vacuum ultraviolet light" or "non-VUV light" refers to deep ultraviolet light, ultraviolet light, visible light, infrared light, or any combination thereof. Generally, the term non-VUV light refers to any light having a wavelength greater than about 190 nm. In addition, the term "near vacuum ultraviolet light" or "near VUV light" is used to refer to light having a wavelength of about 190 nm to about 200 nm (e.g., about 193 tun), which is partially transmissive in the atmosphere. VUV light, non- VUV light, and near VUV light may be monochromatic, near monochromatic, polychromatic, or broadband light.

The terms "first" and "second" as used herein are not to be construed as sequential, temporal, or preferential indicators. Instead, the terms first and second are used to identify different light sources, different measurement subsystems, etc.

Turning now to the drawings, it is noted that the figures presented herein are not drawn to scale. In particular, the scale of some of the elements of the figures is greatly exaggerated to emphasize characteristics of the elements. It is also noted that the figures are not drawn to the same scale. Elements shown in more than one figure that may be similarly configured have been indicated using the same reference numerals.

As described further above, a "see-thru" lamp configuration has been used to combine light from multiple light sources into a single optical path. One example of a see-thru lamp is illustrated in FIG. 1. As shown in FIG. 1, the see-thru lamp includes deuterium ($D_2$) lamp 10. The deuterium lamp is used to provide light that is suitable for measurements in the VUV wavelength regime. The deuterium lamp has a see-thru configuration such that light from fiber 12 can be directed through the deuterium lamp. For example, the deuterium lamp may be configured such that a portion of the lamp, across an entire thickness of the lamp, is substantially transparent to light from fiber 12. In particular, the deuterium lamp may include a "window" that is transparent to light from fiber 12 in place of portions of the deuterium lamp that would normally be opaque or absorbing with respect to light from fiber 12.

Fiber 12 may be coupled to a non-VUV light source such as a xenon (Xe) arc lamp (not shown). Although a Xe arc lamp may generate light having wavelengths in the VUV range, the light that is generated by the Xe arc lamp in this wavelength regime is usually not bright enough for measurements. Therefore, the Xe arc lamp may be used for measurements in non-VUV wavelengths regimes such as the ultraviolet (UV), visible, and near infrared (NIR) wavelength regimes. Other light sources may be used in place of the Xe arc lamp such as a tungsten lamp.

Figure 2:
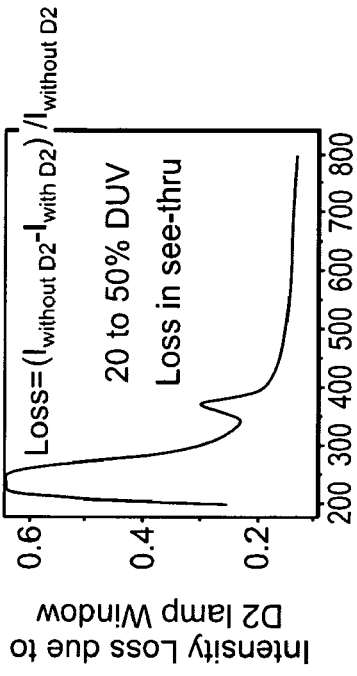
FIG. 2 is a plot illustrating intensity as a function of wavelength for a see-thru lamp.

The see-thru lamp configuration is generally effective for combining light from multiple light sources even though it does have several disadvantages. For example, the see-thru lamp configuration adds complexity to a measurement system since additional imaging optics are necessary. In addition, the see-thru lamp configuration results in a loss in intensity in the deep ultraviolet (DUV) range of wavelengths. For example, as shown in FIG. 2, which illustrates intensity loss due to the deuterium lamp window as a function of wavelength, the deuterium lamp window may cause a 20% to 50% loss in DUV intensity. Therefore, the see-thru lamp may have reduced throughput and increased measurement inaccuracy in the DUV region, which is a region in which measurements are often performed. Furthermore, see-thru lamps are relatively expensive in comparison to other light sources.

Figure 3:
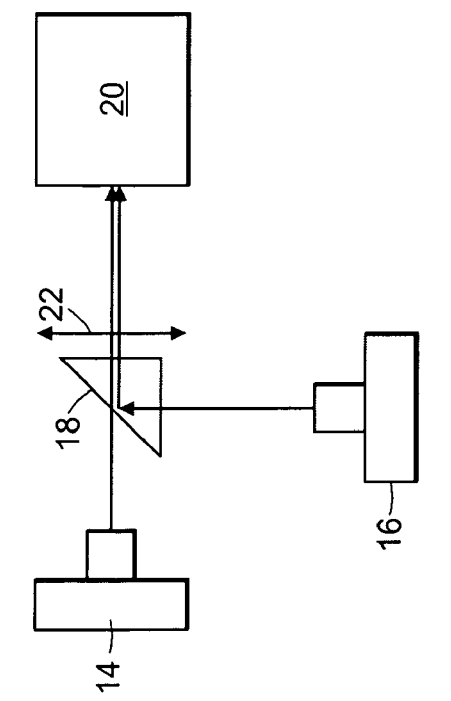
FIGS. 3 and 4 are schematic diagrams illustrating side views of different embodiments of an illumination subsystem configured to provide illumination for a measurement system.

Due to these and other drawbacks of the see-thru lamp configuration and the lack of a different broadband light source that can provide light across wavelengths from VUV to NIR, a novel illumination subsystem has been developed that can be used to provide illumination for a measurement system. FIG. 3 illustrates one such illumination subsystem. As shown in FIG. 3, the illumination subsystem includes first light source 14 and second light source 16. The first and second light sources are configured to generate light for measurements in different wavelength regimes. For example, the first light source may be a xenon arc lamp or another light source that can be used to provide light that is suitable for measurements in non-VUV wavelength regimes (e.g., UV light, visible light, NIR light, or a combination thereof). The second light source may be a deuterium lamp or another light source that can be used to provide light that is suitable for measurements in the VUV wavelength regime.

The first and second light sources may also vary from those described above as long as, in combination, the different wavelength regimes of the two light sources span a relatively wide range of wavelengths (e.g. from a VUV wavelength to an NIR wavelength). In this manner, either one of the first and second light sources may be configured to generate VUV light for the measurements, and the other light source may be configured to generate UV light, visible light, NIR light, or a combination thereof.

As further shown in FIG. 3, the illumination subsystem includes total internal reflection (TIR) prism 18. TIR prism 18 is configured to be moved into and out of an optical path from the first and second light sources to measurement system 20. The TIR prism may be moved into and out of the optical path in the direction shown by arrow 22. The TIR prism may be moved into and out of the optical path using any suitable components known in the art such as a sliding stage (not shown).

By moving the prism in and out of the optical path, a specific light source can be selected for measurements. For example, if the TIR prism is positioned in the optical path, as shown in FIG. 3, light from the second light source is directed along the optical path to measurement system 20. This position of the TIR prism prevents light from first light source 14 from being directed along the optical path to the measurement system. If the TIR prism is positioned out of the optical path (not shown), light from only the first light source is directed along the optical path to measurement system 20. In other words, if the TIR prism is not placed in the optical path, the TIR prism will not interfere with the light from first light source. Any light from second light source 16 that interacts with the TIR prism in this non-optical path position will not be directed to the measurement system.

In this manner, the illumination subsystem may be configured to sequentially provide light from different light sources to a measurement system. In addition, although two light sources are shown in FIG. 3, it is to be understood that light from more than two light sources may be combined in a single optical path in a similar manner. Furthermore, the TIR prism in this and all other embodiments described herein may be replaced with a different optical component that can perform the same function such as an optical lattice having a bend of, for example, 90 degrees or any other appropriate angle known in the art.

TIR occurs when the angle of incidence is more than the critical angle $\sin^{-1}(n_2/n_1)$. Under these conditions, the reflectivity is 1 and has no polarization dependence. Therefore, the material of the prism and the apex angle of the prism should be chosen such that the angle of incidence on the reflecting surface is greater than the critical angle. For the UV-visible spectrum, a 45 degree fused silica prism is a good candidate for the TIR prism. As such, the TIR prism may, in one embodiment, include a 45 degree fused silica prism. However, the configuration of the TIR prism may vary depending on the wavelengths of light it will be used to reflect.

Preferably, the TIR prism introduces substantially no residual polarization to the light from the second light source. Therefore, after interacting with the TIR prism, the polarization of the light will not be substantially altered. In some polarization sensitive measurements like ellipsometry or reflectometry, it is important to not introduce residual polarization to the light used for the measurements. Even though the TIR prism may cause a strong wavelength dependent incident polarization dependent phase change in the reflected light, this phase change is not relevant in ellipsometry or reflectometry measurements since the light source is usually incoherent.

The illumination subsystem shown in FIG. 3 may, therefore, be particularly useful for ellipsometry and/or reflectometry based measurement systems. In addition, measurement system 20 may be configured to perform spectroscopic measurements. In one such embodiment, the measurement system may be configured to perform spectroscopic ellipsometry (SE) measurements. In an additional embodiment, the measurement system may be configured to perform rotating polarizer spectroscopic ellipsometry (RPSE) measurements. Alternatively, the measurement system may be configured to perform spectroscopic reflectometry (SR) measurements. The measurement system may include any measurement system known in the art that can be used to perform SE, RPSE, and/or SR measurements. In addition, the measurement system may be configured as described herein.

The illumination subsystem may also be included in the optical subsystems described in U.S. patent application Ser. No. 10/845,958 filed May 14, 2004, entitled "Systems and Methods for Measurement of a Specimen with Vacuum Ultraviolet Light" by Fielden et al., which is incorporated by reference as if fully set forth herein. In addition, the illumination subsystem and the measurement system may be disposed in a suitable environment for VUV measurements. For example, the illumination subsystem and the measurement system may be disposed in a purged environment surrounding at least the optical path of the VUV light. Examples of systems that can provide suitable environments for VUV measurements are also described in the Patent Application by Fielden et al. that is incorporated by reference above. An additional example of a system that can provide a suitable environment for VUV measurements is described further below.

Figure 4:
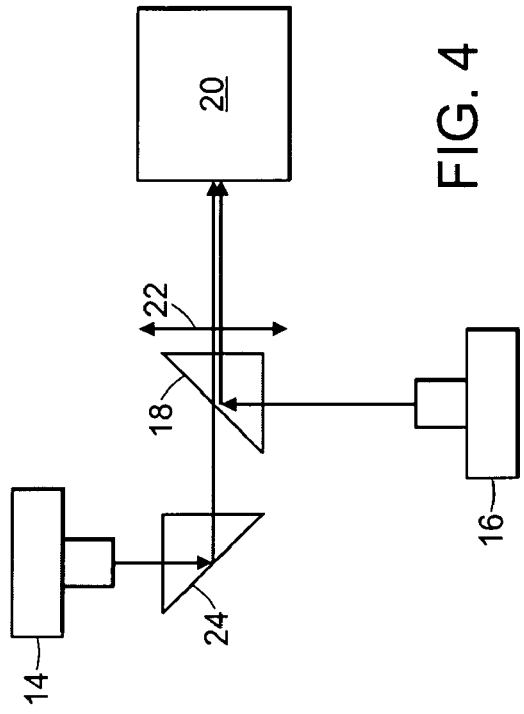

In some embodiments, the illumination subsystem may include an additional TIR prism that is configured to direct the light from the first light source along the optical path. One example of such an illumination subsystem is illustrated in FIG. 4. As shown in FIG. 4, additional TIR prism 24 is positioned in the optical path from the first light source to the measurement system. In one embodiment, the additional TIR prism may have a stationary position in the optical path. Alternatively, the additional TIR prism may be moved into and out of the optical path as described above. Additional TIR prism 24 is configured to direct light from first light source 14 to measurement system 20. Like the illumination subsystem described above, this illumination subsystem may be used to select which light source is used by measurement system 20 for measurements. For instance, if TIR prism 18 is positioned in the optical path, only light from second light source 16 may be directed to the measurement system. Alternatively, if TIR prism 18 is positioned out of the optical path, only light from first light source 14 that is reflected by TIR prism 24 is directed to the measurement system. In this manner, light from different light sources may be directed to the measurement system sequentially. In addition, light of more than two light sources may be combined into a single optical path in a similar manner (e.g., using a different TIR prism for each of the light sources).

TIR prism 24 may be selected as described above based on the critical angle. In addition, preferably, additional TIR prism 24 introduces substantially no residual polarization to the light from the first light source. In this manner, the illumination subsystem may be particularly useful for providing light for ellipsometry and/or reflectometry based measurement systems as described above. The additional TIR prism may also allow for a reduction in the size of the illumination subsystem. In particular, the size of the measurement system may be reduced since light from all of the light sources can be folded using TIR prisms. Reducing the size of the measurement system may allow the measurement system to be integrated into a process tool.

Figure 5:
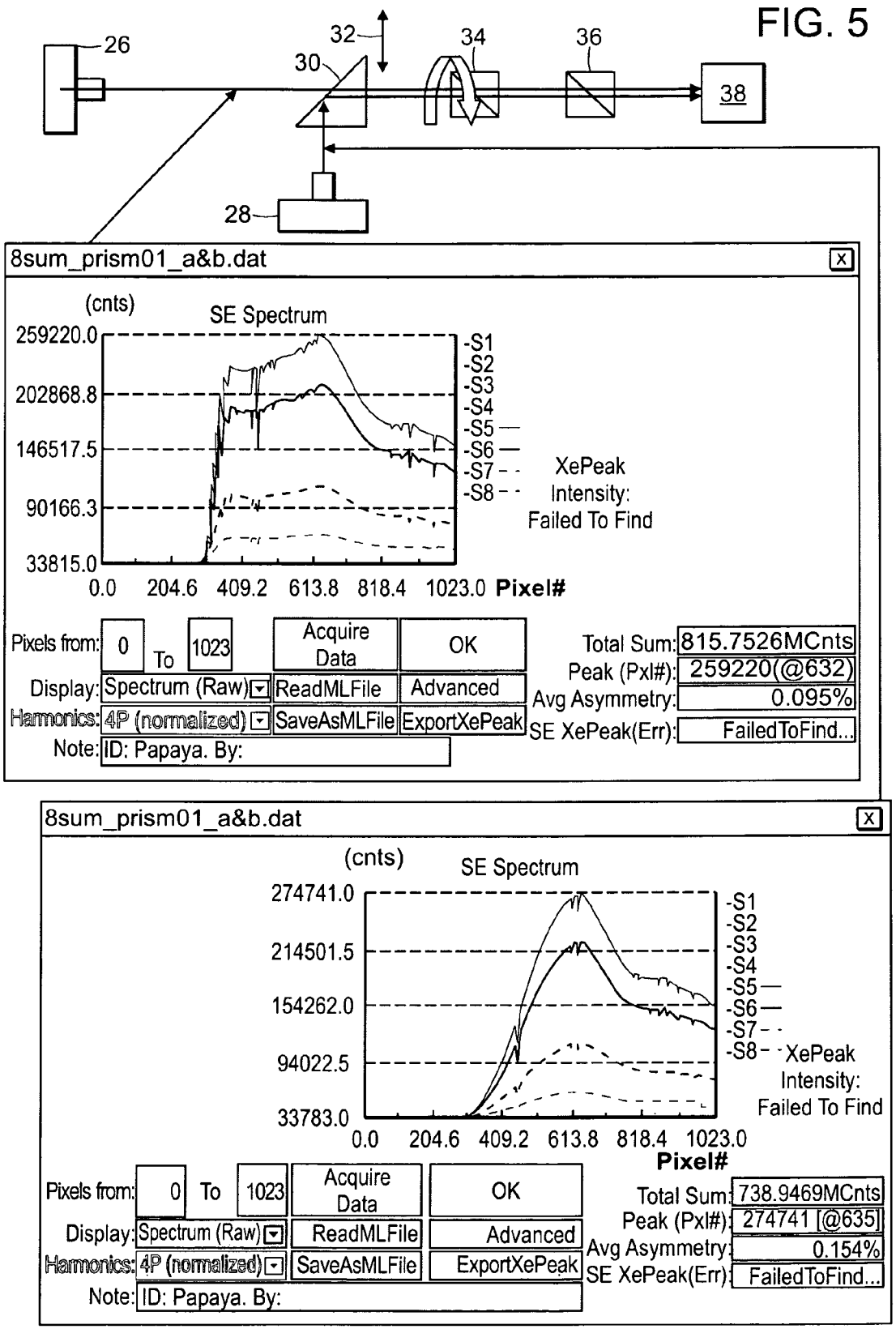
FIG. 5 is a schematic diagram illustrating a side view of a system that was used to measure residual polarization of light caused by an embodiment of an illumination subsystem and plots illustrating the measurements of the residual polarization.
Figure 6:
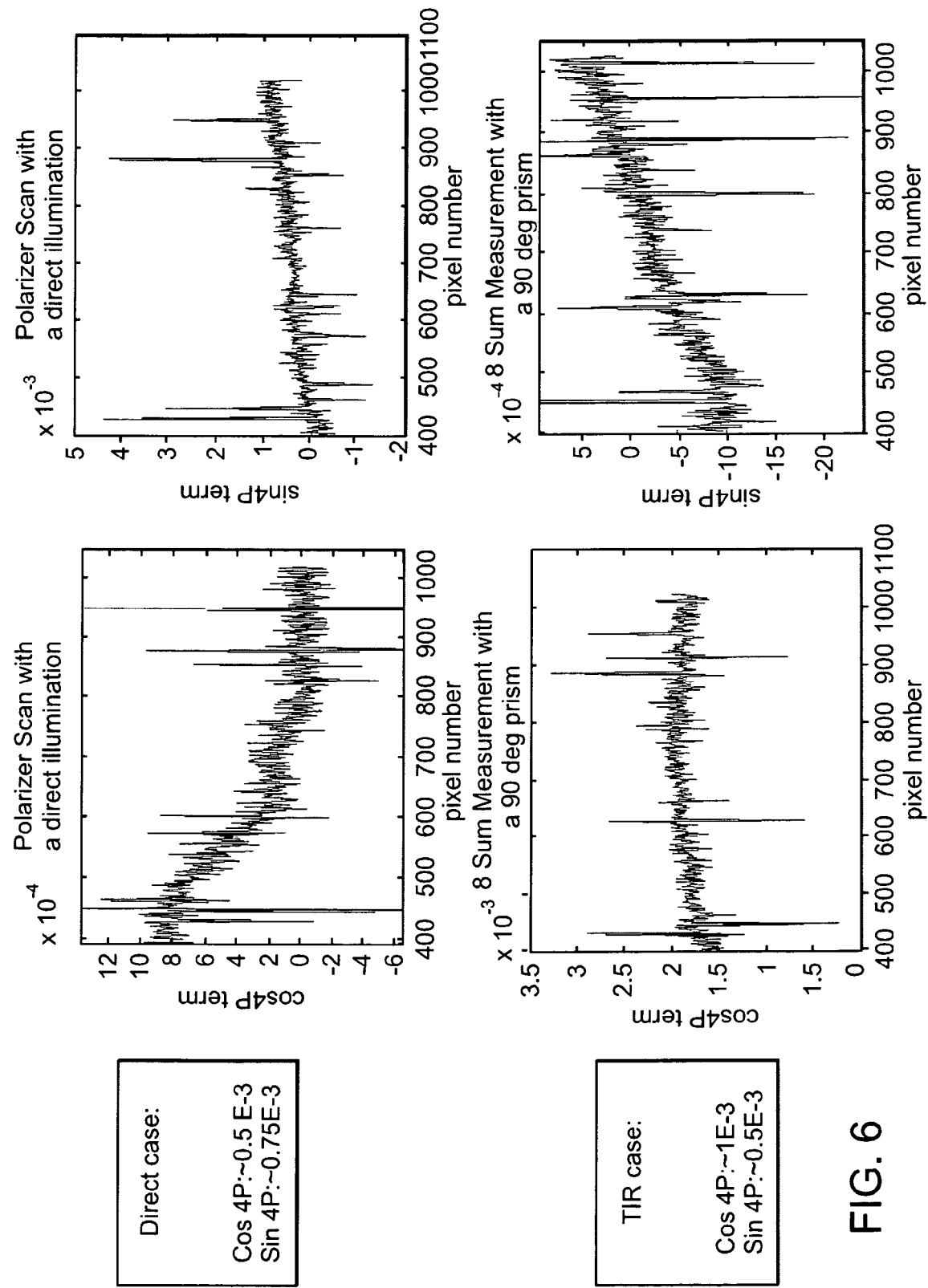
FIG. 6 includes a number of plots illustrating results of experiments showing that both direct illumination and total internal reflection (TIR) illumination have equivalent 4P harmonics.

Experimentally, this TIR based configuration for combining light from different light sources into a single optical path was examined by measuring residual polarization of the light. The schematic of the experiment is shown in FIG. 5. The experiment was performed using $D_2$ lamps 26 and 28. However, the experiment may also be performed using any other light sources (e.g., Xenon arc lamps). When fused silica TIR prism 30 was moved out of the optical path in the direction shown by arrow 32, light from $D_2$ lamp 26 passed through rotating polarizer 34 and analyzer 36 and was detected by spectrometer 38. When fused silica TIR prism 30 was positioned in the optical path, as shown in FIG. 5, light from $D_2$ lamp 28 reflected by TIR prism 30 passed through polarizer 34 and analyzer 36 and was detected by spectrometer 38. In this manner, the polarization state of both types of illumination, TIR and direct (non-TIR), were measured with a rotating polarizer ellipsometry (RPE) configuration. This configuration is a simple cross polarization configuration. Complete modulation is expected if there is no residual polarization. If any residual polarization is caused by TIR, it will be shown in the higher harmonic terms in the RPE measurements. The results showed that both direct illumination and TIR illumination have equivalent 4P harmonics, as shown in FIG. 6, thereby demonstrating the feasibility of the TIR based illumination subsystems described herein. A deuterium lamp was used to generate the results shown in FIG. 6, but the preferred approach is to use Xe lamp radiation and fused silica prisms in order to be more cost effective.

The illumination subsystem embodiments described herein have many advantages over other currently used illumination subsystems such as the see-thru lamp configuration described above. For instance, as described above, light from several light sources can be combined into a common optical path without creating residual polarization in the light. In addition, the illumination subsystems described herein have a higher throughput particularly in the DUV regime. The illumination subsystems described herein can also be modular. For example, the light sources are independent of each other. This configuration also has much less complexity and more flexibility compared to the see-thru configuration. In addition, the lifetime of one light source does not depend on the other light source. For instance, window contamination limits lamp lifetime in the arc lamp cases. In the see-thru lamp configuration, the lifetime of one lamp can affect the lifetime of the other lamp. Furthermore, the optical paths can be folded in the embodiments described herein, which results in a smaller system. In contrast, the see-thru lamp has additional imaging optics, which are used to image one lamp into a see-thru portion of another lamp. This optical configuration will result in an even longer illuminator. Moreover, the cost of the illumination subsystems described herein will be much lower than the see-thru lamp.

The TIR-based optical configuration described above may also be implemented in the detection side of a measurement system. For instance, when measurements are to be performed across a broad spectral range (e.g., from VUV to NIR), different detectors (e.g., spectrometers) may be used to perform measurements in different wavelength regimes. In such a configuration, a TIR prism may be used to separate the light returned from the specimen into different optical paths to the different detectors. Such an optical configuration is described further herein.

Figure 7:
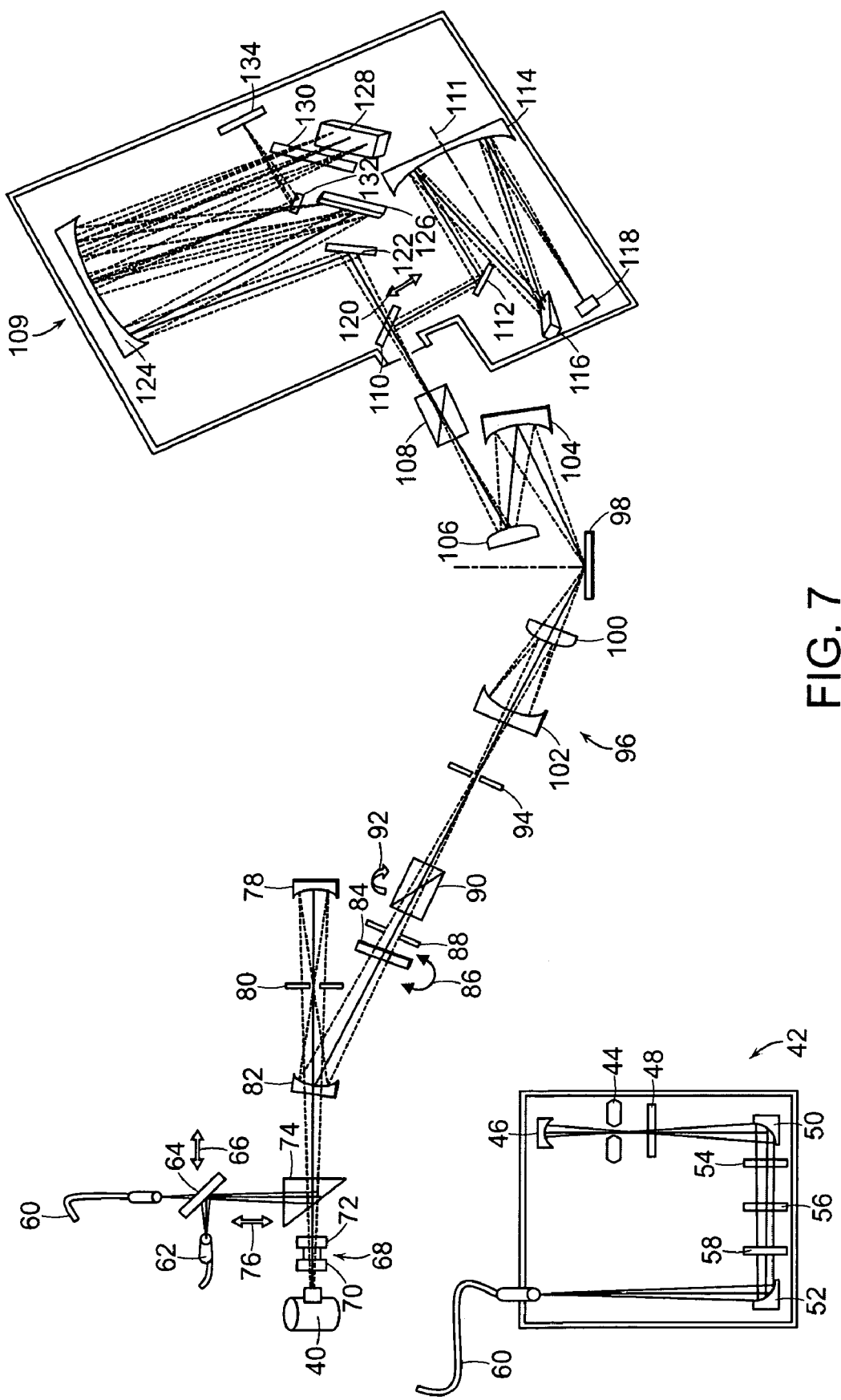
FIGS. 7-10 are schematic diagrams illustrating side views of different to embodiments of a measurement system that include different embodiments of an illumination subsystem.

FIG. 7 illustrates a measurement system coupled to an illumination subsystem, which may be configured as described above. The measurement system shown in FIG. 7 is configured as a BBSE. The illumination subsystem includes deuterium lamp 40. The deuterium lamp may be used as a VUV light source. Alternatively, the illumination subsystem may include any other VUV light source known in the art.

The illumination subsystem includes more than one light source. For example, the illumination subsystem may include Xe lamp illuminator 42. The Xe lamp illuminator includes Xe lamp 44, rear mirror 46, heat sink window 48, and coupling mirrors 50 and 52. In addition, the Xe lamp illuminator may include a number of components disposed between coupling mirrors 50 and 52 such as shutter 54, filter wheel 56, and UV flip-in filter 58. Light from coupling mirror 52 is directed to optical fiber 60. The Xe lamp illuminator may be used for measurements at wavelengths greater about than about 200 nm. Although the Xe lamp may generate light at wavelengths less than 200 nm, this light is usually not high enough in intensity to provide a useful signal for measurements.

The optical subsystem may also include a mercury (Hg) lamp (not shown), which may be used to provide light for measurements at a variety of wavelengths such as 185 nm, 254 nm, 280 nm, 365 nm, 420 nm, 502 nm, and 540 nm. Optical fiber 62 may be coupled to the Hg lamp and may direct light from the Hg lamp to slide mirror 64. The illumination subsystem may also include any other useful light sources known in the art.

The illumination subsystem may also include a number of components to control the wavelengths of light that are directed to the specimen for various measurements. For example, shutter 54 may be closed if measurements are not being made with light from the Xe lamp. In another example, filter wheel 56 and UV flip-in filter 58 may be used to filter certain wavelengths of the Xe lamp such that light having selected wavelengths may be used for measurements. In yet another example, if measurements are being made with light from the Hg lamp, then slide mirror 64 may be positioned as shown in FIG. 7 such that light from the Hg lamp can be directed to the specimen (by other components as described herein). However, if measurements are not being made with light from the Hg lamp, then the slide mirror may be moved out of the optical path of the illumination subsystem in the direction shown by arrow 66 such that light from the Hg lamp is not directed to the specimen. Slide mirror 64 can also be configured to transmit light from optical fiber 60. In this manner, slide mirror 64 in the position shown in FIG. 7 allows light from both of the optical fibers to be used by the optical subsystem at the same time. Alternatively, the slide mirror may be configured to absorb or reflect light from optical fiber 60. In this configuration, when the slide mirror is in the position shown in FIG. 7, light from the Xe lamp will be blocked, and light from the Hg lamp will be provided to other components of the measurement system for measurements.

The illumination subsystem shown in FIG. 7 also includes system 68. System 68 is coupled to deuterium lamp 40. System 68 is configured to control an intensity of VUV light in the measurement system. In particular, system 68 includes a cell, portions 70 and 72 of which are positioned in the optical path of the deuterium lamp. Portions 70 and 72 are substantially transparent to the VUV light. System 68 also includes a flow subsystem (not shown). The flow subsystem is configured to control an amount of one or more gases in the cell to control the intensity of the VUV light that exits the cell. For example, the flow subsystem may supply a first gas and a second gas to the cell. The first gas is substantially transparent to the VUV light, and the second gas absorbs the VUV light. In another example, the flow subsystem may be configured to create a vacuum in the cell. In this manner, the flow subsystem may alter the intensity of the VUV light (e.g., by altering its VUV transmission between (and including) about 100% transmission and about 0% transmission) by altering the gas or the vacuum conditions in the cell. System 68 may be further configured as described in U.S. patent application Ser. No. 11/058,539 entitled "Systems and Methods for Controlling an Intensity of Vacuum Ultraviolet Light in an Optical Subsystem" by Kwak et al. filed on Feb. 14, 2005, which is incorporated by reference as if fully set forth herein.

The illumination subsystem shown in FIG. 7 also includes total internal reflectance (TIR) prism 74. The position of TIR prism 74 may be altered depending on the light source that is being used for measurements as described above. For example, in the position shown in FIG. 7, TIR prism 74 directs light from optical fiber 62 to other optical components of the measurement system such that measurements can be made with light from the Hg lamp. If slide mirror 64 transmits light from optical fiber 60, then the TIR prism may also direct light from optical fiber 60 to other optical components of the measurement system such that measurements can also be made with light from the Xe lamp. In the position shown in FIG. 7, the TIR prism does not transmit light that exits system 68. Therefore, light from the deuterium lamp cannot be used for measurements while measurements are being performed with light from the Hg lamp (and possibly the Xe lamp). However, TIR prism 74 may be moved in the direction illustrated by arrow 76 out of the optical path of the light exiting system 68. While the TIR prism is in this position (not shown), light exiting system 68 will be directed to other optical components of the measurement system such that measurements can be made with this light. While measurements are being made with light from the deuterium light source, measurements cannot be made with light from the Hg lamp and the Xe lamp. In this manner, the TIR prism can be configured to combine light from multiple light sources into a common optical path.

The illumination subsystem, therefore, provides rapid sequential measurements in various spectral ranges including non-VUV and VUV. The light that will be used for measurements is directed from either TIR prism 74 or system 68 to optical components of the measurement system such as coupling mirror 78, which directs the light to plate 80. Light that passes through the pinhole in plate 80 is directed to coupling mirror 82, which directs the light to VUV absorption filter 84. As described above, the intensity of the VUV light from deuterium lamp 40 is controlled by system 68. In addition, during VUV measurements with light from the deuterium lamp, VUV absorption filter 84 may be moved out of the optical path of the optical subsystem in the direction indicated by arrow 86.

Light transmitted by VUV absorption filter 84, if included in the system, is directed to plate 88. Light that passes through the aperture in plate 88 is directed to polarizer 90. Polarizer 90 may rotate in the direction shown by arrow 92. In this manner, the measurement system shown in FIG. 7 may be configured as an RPSE. The polarizer may include any suitable polarizing component known in the art such as a Rochon prism. Light transmitted by the polarizer is directed to plate 94. Light that passes through the aperture in plate 94 is directed to focusing subsystem 96, which is configured to focus the light onto specimen 98. In the example shown in FIG. 7, the light is directed to the specimen at an oblique angle of incidence.

However, the light may be directed to the specimen at other angles of incidence depending on, for example, the measurements that are being performed by the measurement system. Light that passes through the aperture in plate 94 is directed by mirror 100 to focusing mirror 102. Focusing mirror 102 focuses the light to a measurement spot on specimen 98.

Light reflected from specimen 98 is collected by a collection subsystem that includes collection mirror 104 and mirror 106. Mirror 106 directs the collected light to analyzer 108, which in this example is a non-rotating polarizing component. The analyzer may be any suitable polarizing component known in the art. Light transmitted by analyzer 108 is directed to slide mirror 110. In the position of slide mirror 110 shown in FIG. 7, the light from the analyzer is directed to prism-based portion 111 of spectrometer 109. The prism-based portion of the spectrometer can be used to measure the intensity of the light at wavelengths from about 150 nm to about 300 nm (i.e., in the VUV and DUV range). Obviously, the prism-based portion of the spectrometer may be used to measure the intensity of light at wavelengths across this entire wavelength range, across only a portion of the wavelength range, or at one or more specific wavelengths within this range depending on the light source being used (or wavelengths selected) for the measurements.

The light directed by slide mirror 110 to the prism-based portion of the spectrometer is directed by folding mirror 112 to focusing mirror 114, which directs the light to prism 116. The prism may be formed of a material that is substantially transparent to VUV light. For example, the prism may be formed of calcium fluoride. The prism is configured to separate the light according to wavelength and directs the light back to focusing mirror 114. Focusing mirror 114 directs the light to detector 118. Detector 118 is configured to measure the intensity of the light at each of the wavelengths at which measurements are being performed. Detector 118 may include a charge coupled device (CCD) type detector or any other suitable array detector known in the art.

The spectrometer also includes a grating-based portion, which can be used to measure the intensity of the light at wavelengths from about 210 nm to about 900 nm (i.e., from DUV to IR wavelengths). In this manner, the measurement system may be a dual spectrometer system. Obviously, the grating-based portion of the spectrometer may be used to measure the intensity of light at wavelengths across this entire wavelength range, across only a portion of the wavelength range, or at one or more specific wavelengths within this range depending on the light source being used (or wavelengths selected) for the measurements. Light collected by the collection subsystem may be directed to the grating-based portion of the spectrometer when slide mirror 110 is moved out of the optical path of the optical subsystem in the direction indicated by arrow 120.

When the slide mirror is positioned out of the optical path of the light from analyzer 108, the light is directed from the analyzer to folding mirror 122. Folding mirror 122 directs the light to focusing mirror 124, which directs the light to grating 126. Grating 126 is configured to separate the light according to wavelength and directs the separated light back to focusing mirror 124. Grating 126 may include any suitable diffraction grating known in the art. Focusing mirror 124 directs the light to detector 128, which is configured to measure the intensity of the light at each of the wavelengths at which measurements are being performed. Detector 128 may be a CCD type detector or any other suitable detector known in the art.

In some embodiments, the spectrometer may include filter 130. Filter 130 may be configured to filter orders of the light except those at which measurements are to be made. In this manner, the filter may reduce spectral overlap between high order of UV spectrum and $1^{st}$ order of Visible and IR spectrum of the measurements performed by detector 128. Filter 130 may include any suitable optical component known in the art.

The measurement system illustrated in FIG. 7 may also include a number of other optical components. For example, the spectrometer may include folding mirror 132. Focusing mirror 124 may be configured to direct a portion of the light from grating 126 to folding mirror 132. Folding mirror 132 is configured to direct the light to detector 134. The detector may be used as a fine focusing detector (i.e., to monitor the focusing of light on specimen 98 by focusing subsystem 96). Detector 134 may include any suitable detector known in the art such as a position sensitive detector. The measurement system may also include a number of other components (not shown) such as a scanning subsystem.

As described above, the measurement system shown in FIG. 7 is advantageous in that it provides rapid, sequential measurements in multiple spectral ranges. The measurement system may have a number of additional advantages. For example, spherical optics can be used in the measurement system for better image quality and box size. In addition, the system may have near-exact phase cancellation due to the four mirror optical configuration.

In addition, each of the detectors included in the measurement system may be coupled to a processor (not shown) via a transmission medium and optionally one or more electronic components such as analog-to-digital converters. The processor may be configured to perform a number of functions on the signals generated by the detectors. For example, the processor may be configured to evaluate the focusing of the measurement system using signals from detector 134 and may be configured to control one or more components of the system such as focusing subsystem 96 to alter the focusing of the system. In addition, the processor may be configured to determine ellipsometric parameters from the signals generated by detectors 118 and 128. The processor may also use these signals or the ellipsometric parameters to determine one or more characteristics of the specimen such as a thickness of a film on the specimen, critical dimensions of patterned features on the specimen, overlay of the specimen, dimensions of defects on the specimen, etc.

Figure 8:
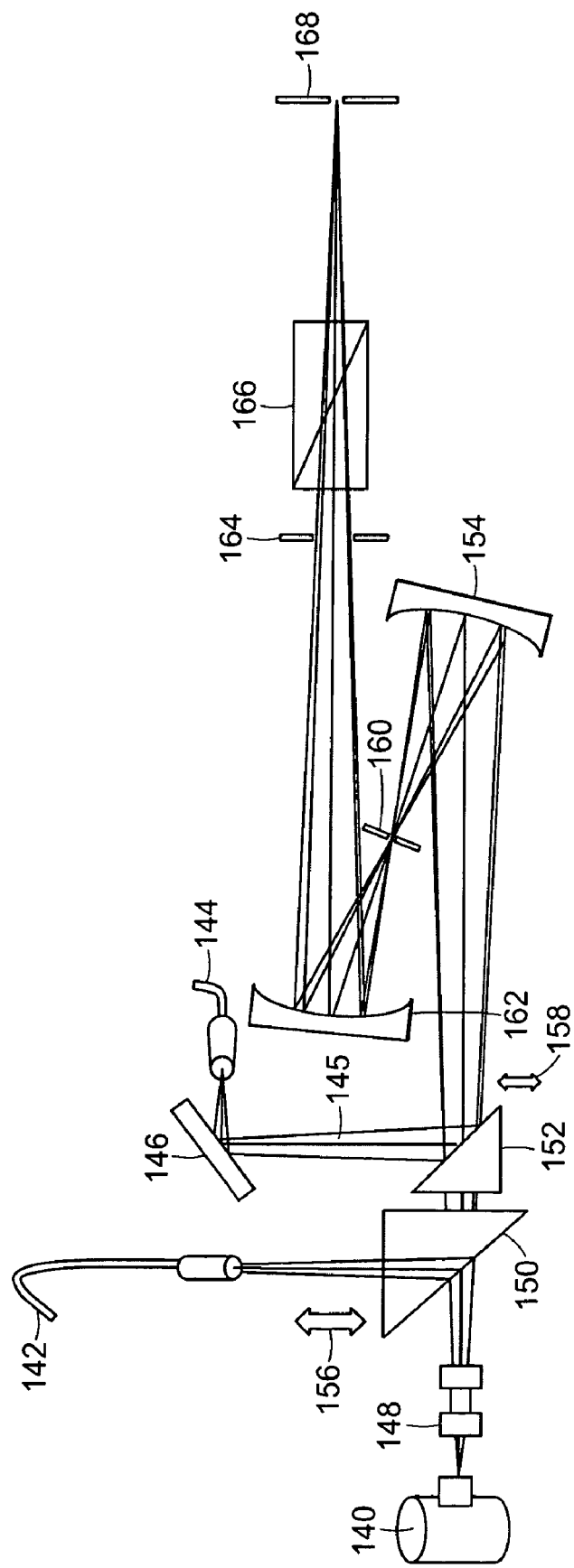

FIG. 8 illustrates an illumination subsystem that may be coupled to additional optical components (not shown) in a measurement system such that the measurement system can be used for performing measurements on a specimen. For example, the illumination subsystem shown in FIG. 8 may be configured to direct light to a focusing subsystem such as focusing subsystem 96 shown in FIG. 7. The illumination subsystem shown in FIG. 8 may be coupled to a number of other optical components of the measurement system shown in FIG. 7 such as analyzer 108 and spectrometer 109. In addition, the illumination subsystem illustrated in FIG. 8 may be configured as a SE or any other optical subsystem known in the art.

The illumination subsystem shown in FIG. 8 includes deuterium lamp 140. The deuterium lamp may be used as a VUV light source. Alternatively, the illumination subsystem may include any other VUV light source known in the art. The illumination subsystem may include more than one light source. For example, the illumination subsystem may include a Xe lamp illuminator (not shown). The Xe lamp illuminator may be configured as described above. Light from the Xe lamp illuminator is directed to optical fiber 142. As described above, the Xe lamp illuminator may be used for measurements at wavelengths greater than about 200 nm. The illumination subsystem may also include an Hg lamp (not shown), which may be used to provide light for measurements at a variety of wavelengths such as those listed above. Optical fiber 144 may be coupled to the Hg lamp and may direct light from the Hg lamp to folding mirror 146. The illumination subsystem may also include any other useful light sources known in the art.

The illumination subsystem may also include a number of components configured to control the wavelengths of light that are directed to the specimen for various measurements. For example, as described above, the Xe lamp illuminator may include a number of components that may be used to control the wavelengths of light from the Xe lamp that exit the Xe lamp illuminator. In addition, the illumination subsystem shown in FIG. 8 also includes system 148. System 148 is coupled to deuterium lamp 140. System 148 is configured to control an intensity of VUV light in the illumination subsystem by altering the intensity of the VUV light generated by deuterium lamp 140. System 148 may be further configured as described in the Patent Application by Kwak et al., which is incorporated by reference as if fully set forth herein. For example, system 148 may include a cell and a flow subsystem, both of which may be configured as described in this patent application.

The illumination subsystem shown in FIG. 8 also includes TIR prism 150. The position of TIR prism 150 may be altered depending on the light source that is being used for measurements. For example, in the position shown in FIG. 8, TIR prism 150 blocks light from system 148 coupled to deuterium lamp 140. However, TIR prism 150 directs light from optical fiber 142 to other components of the illumination subsystem. For example, if TIR prism 152 was not in the position illustrated in FIG. 8, TIR prism 150 would direct light from optical fiber 142 to mirror 154. TIR prism 150 may be moved in the direction indicated by arrow 156 such that TIR prism 150 is positioned out of the optical path of the light from system 148. In this manner, light from system 148 can be directed to mirror 154, and light from optical fiber 142 if reflected by TIR prism 150 would not be directed to other optical components of the measurement system. Therefore, measurements can be performed with light from the deuterium lamp or with light from the Xe lamp illuminator depending on the positions of TIR prisms 150 and 152.

The position of TIR prism 152 can also be altered depending on the light source that is being used for measurements. For example, in the position shown in FIG. 8, TIR prism 152 directs light 145 from mirror 146 (coupled to the Hg lamp by optical fiber 144) to other optical components of the measurement system such that measurements can be made with light from the Hg lamp. In the position shown in FIG. 8, TIR prism 152 does not transmit light that exits system 148 or light reflected from TIR prism 150. Therefore, light from the deuterium lamp and the Xe lamp illuminator cannot be used for measurements while measurements are being performed with light from the Hg lamp. However, TIR prism 152 may be moved in the direction illustrated by arrow 158 out of the optical path of the light exiting system 148 or the light reflected by TIR prism 150. In this position of TIR prism 152, light from the deuterium light source or light from the Xe lamp illuminator (depending on the position of TIR prism 150) will be directed to other optical components of the measurement system such that measurements can be made with this light.

The light that will be used for measurements is directed from either TIR prism 150, TIR prism 152, or system 148 to coupling mirror 154, which directs the light to plate 160. Light that passes through the pinhole in plate 160 is reflected by mirror 162, which directs the light to plate 164. Light that passes through the aperture in plate 164 is directed to polarizer 166. Polarizer 166 may be configured as described above. Light transmitted by the polarizer is directed to plate 168. Light that passes through the aperture in plate 168 may be directed to a focusing subsystem such as the focusing subsystem shown in FIG. 7. The illumination subsystem and measurement system shown in FIG. 8 may be further configured as described herein. In addition, the illumination subsystem may be further configured as described in the Patent Application by Kwak et al. that is incorporated by reference above.

The illumination subsystem shown in FIG. 8 includes, therefore, a BBSE illuminator design based on combining several light paths into a common optical path. In addition, as described above, the light is combined into a common optical path without residual polarization in the light due to the use of the TIR prisms. In addition, the illumination subsystem has several advantages particularly in comparison to the see-thru lamp in that the illumination subsystem shown in FIG. 8 has a higher throughput, little to no loss of ultraviolet light, lower cost, and modularity.

Figure 9:
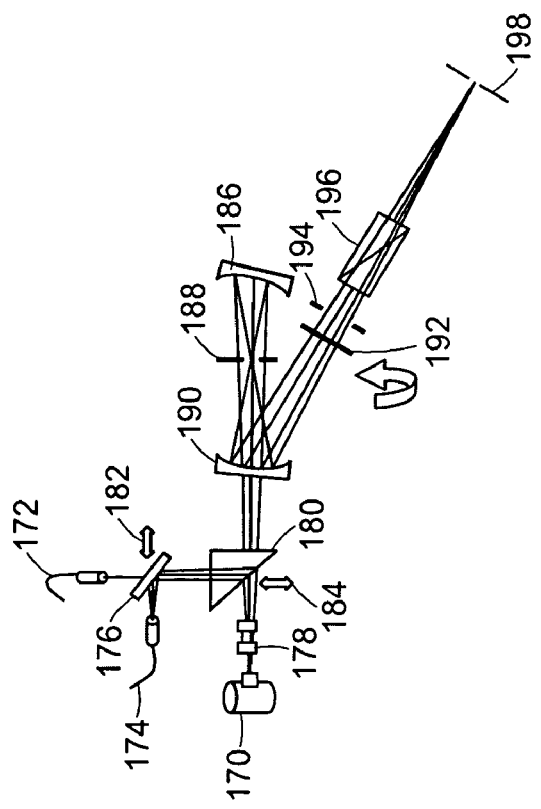

FIG. 9 illustrates another example of an illumination subsystem, which may be coupled with additional optical components (not shown) of a measurement system. For example, the illumination subsystem shown in FIG. 9 may be configured to direct light to a focusing subsystem such as focusing subsystem 96 shown in FIG. 7. The illumination subsystem shown in FIG. 9 may include a number of other optical components of the measurement system shown in FIG. 7 such as analyzer 108 and spectrometer 109. In addition, the illumination subsystem illustrated in FIG. 9 may be used in a BBSE or any other optical subsystem known in the art.

The illumination subsystem shown in FIG. 9 includes deuterium lamp 170. The deuterium lamp may be used as a VUV light source. Alternatively, the illumination subsystem may include any other VUV light source known in the art. The illumination subsystem may include more than one light source. For example, the illumination subsystem may include a Xe lamp illuminator (not shown). The Xe lamp illuminator may be configured as described above. Light from the Xe lamp illuminator is directed to optical fiber 172. As described above, the Xe lamp illuminator may be used for measurements at wavelengths greater about than about 200 nm. The illumination subsystem may also include a Hg lamp (not shown), which may be used to provide light for measurements at a variety of wavelengths such as those listed above. Optical fiber 174 may be coupled to the Hg lamp and may direct light from the Hg lamp to folding mirror 176. The illumination subsystem may also include any other useful light sources known in the art.

The illumination subsystem may also include a number of components configured to control the wavelengths of light that are directed to the specimen for various measurements. For example, as described above, the Xe lamp illuminator may include a number of components that may be used to control the wavelengths of light from the Xe lamp that exit the Xe lamp illuminator. In addition, the illumination subsystem shown in FIG. 9 also includes system 178. System 178 is coupled to deuterium lamp 170. System 178 is configured to control an intensity of VUV light in the illumination subsystem by altering the intensity of the VUV light generated by deuterium lamp 170. System 178 may be further configured as described above.

The illumination subsystem shown in FIG. 9 also includes TIR prism 180. The position of TIR prism 180 may be altered depending on the light source that is being used for measurements as described above. For example, in the position shown in FIG. 9, TIR prism 180 blocks light from system 178 coupled to deuterium lamp 170 and directs light from folding mirror 176 to other components of the measurement system. If folding minor 176 is moved out of the optical path of the light from optical fiber 172 in the direction shown by arrow 182, then TIR prism 180 directs light from optical fiber 172 to other components of the measurement system. TIR prism 180 may be moved in the direction indicated by arrow 184 such that TIR prism 180 is positioned out of the optical path of the light from system 178. In this manner, light from system 178 can be directed to mirror 186, and light from optical fiber 172 or 174 if reflected by TIR prism 180 would not be directed to other optical components of the measurement system. Therefore, measurements can be performed with light from the deuterium lamp, the Hg lamp, or Xe lamp illuminator depending on the positions of folding mirror 176 and TIR prism 180.

The light that will be used for measurements is directed from either TIR prism 180 or system 178 to coupling mirror 186, which directs the light to plate 188. Light that passes through the pinhole in plate 188 is reflected by minor 190, which directs the light to VUV absorption filter 192. The VUV absorption filter may be configured as described above. Light that passes through the VUV absorption filter is directed to plate 194. Light that passes through the aperture in plate 194 is directed to polarizer 196. Polarizer 196 may be configured as described above. Light transmitted by the polarizer is directed to plate 198. Light that passes through the aperture in plate 198 may be directed to a focusing subsystem such as the focusing subsystem shown in FIG. 7. The illumination subsystem and measurement system shown in FIG. 9 may be further configured as described herein. In addition, the illumination subsystem may be further configured as described in the Patent Application by Kwak et al. that is incorporated by reference above.

The illumination subsystem shown in FIG. 9 may be modified somewhat to reduce the size of the illumination subsystem. In particular, the illumination subsystem may be "folded" to reduce the size of the illumination subsystem thereby enhancing its compatibility with integration design requirements (i.e., requirements for integration of the measurement system into a process tool). The system may also be particularly useful for BBSE integrated designs and other spectroscopic integrated systems that have a relatively wide range of operating wavelengths (e.g., from about 150 nm to about 900 nm). The compressibility of the illumination subsystem and the broadband capabilities are a direct result of the incorporation of TIR optics.

Figure 10:
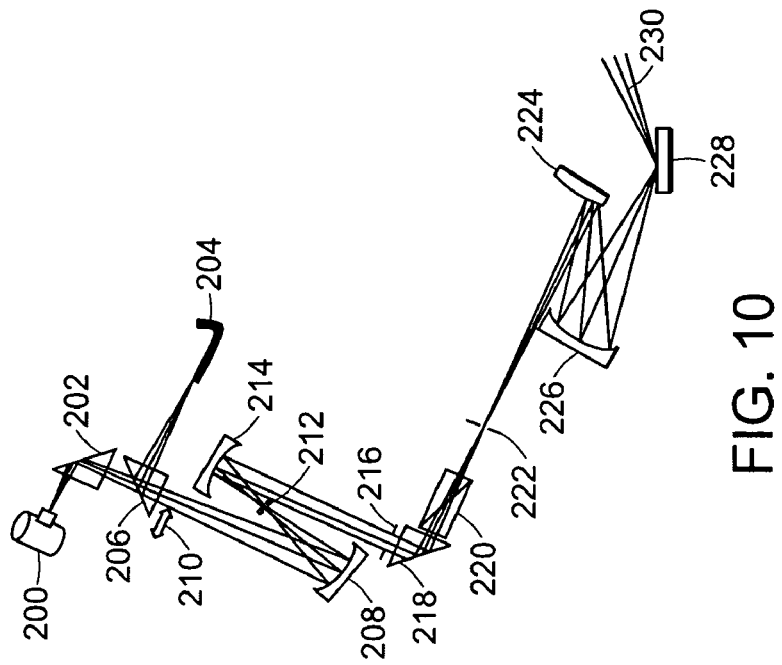

One such "compressed" illumination subsystem is illustrated in FIG. 10. This illumination subsystem includes deuterium lamp 200, which may be configured as described above. Light from deuterium lamp 200 is reflected by TIR prism 202, which may also be configured as described above. The illumination subsystem also includes another light source such as an Xe lamp (not shown). Light from the Xe lamp may be directed by optical fiber 204 to TIR prism 206. As shown in FIG. 10, when TIR prism 206 is positioned in the optical path of the illumination subsystem, only light from optical fiber 204 is directed to coupling mirror 208. However, TIR prism 206 may be moved out of the optical path of the illumination subsystem in the direction shown by arrow 210. When TIR prism 206 is positioned out of the optical path, light from TIR prism 202 is directed to coupling mirror 208. In this manner, the position of TIR prism 206 may be altered to change the light source that is used for measurements.

Light reflected from coupling mirror 208 is directed to plate 212. Light that passes though a pinhole in plate 212 is directed to coupling mirror 214. Light reflected from coupling mirror 214 is directed to plate 216, and light which passes though an aperture in plate 216 is reflected by TIR prism 218 to polarizer 220. Polarizer 220 may be a Rochon prism or any other suitable optical component known in the art. Light exiting polarizer 220 is directed to plate 222. Light that passes through a slit in plate 222 is directed by focusing mirrors 224 and 226 to specimen 228. Light 230 returned from the specimen can be collected by a collection subsystem, which may be configured as described herein. The system shown in FIG. 10 may be further configured as described herein.

Additional embodiments relate to a measurement system that includes two or more measurement subsystems that share a common optical path, but which perform measurements in opposite directions along the common optical path. Due to time-reversal symmetry in linear optical measurements, a counter propagating beam follows exactly the same path as the forward propagating beam. Utilizing this property, a system may include two or more measurement subsystems operating in reverse directions and sharing the same optics. In semiconductor metrology or inspection applications, many optics are involved in the illuminator, focusing, and collection portions of the measurement systems. By sharing the same optics, the cost can be lowered substantially. Furthermore, the matching between the two measurements of the measurement systems can be much better than having two separate measurement heads.

Figure 11:
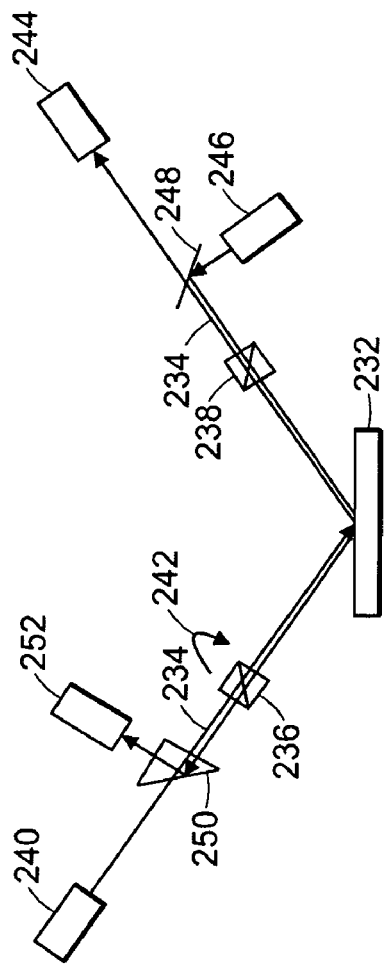

One embodiment of such a measurement system is shown in FIG. 11. The measurement system shown in FIG. 11 includes a first measurement subsystem configured to perform measurements of specimen 232 along optical path 234 in a first direction. The measurement system also includes a second measurement subsystem configured to perform measurement of specimen 232 along optical path 234 in a second direction that is opposite to the first direction. Optical components 236 and 238 positioned in optical path 234 are used by the first and second measurement subsystems for the measurements.

In one embodiment, the first measurement subsystem includes light source 240. Light source 240 directs light to polarizing component 236. In one embodiment, polarizing component 236 may be configured to rotate as shown by arrow 242. The polarizing component may include any suitable polarizing component known in the art. Light exiting polarizer 236 is directed to specimen 232. Light returned from specimen 232 passes through polarizing component 238. In this embodiment, polarizing component 238 may have a stationary position. Polarizing component 238 may include any suitable polarizing component known in the art. Light exiting polarizing component 238 is directed to detector 244. Detector 244 may include any suitable detector known in the art such as a spectrometer. In addition, the detector may be selected based on the wavelengths of light at which measurements will be performed by the detector.

The first measurement subsystem may be configured as an ellipsometer. As such, polarizing component 236 functions as a polarizer for the ellipsometer, and polarizing component 238 functions as an analyzer for the ellipsometer. In this manner, the first measurement subsystem is configured as an RPE. In addition, light source 240 may include a spectroscopic or broadband light source. As such, the measurements performed by the first measurement subsystem may include SE measurements. In addition, the first measurement subsystem may be configured as an RPSE.

Light source 240 may be configured to generate light having UV wavelengths, DUV wavelengths, visible wavelengths, NIR wavelengths, or a combination thereof. For example, light source 240 may be a Xe lamp. In this manner, the first measurement subsystem may be configured to perform the measurements at UV wavelengths, DUV wavelengths, visible wavelengths, NIR wavelengths, or a combination thereof. Alternatively, light source 240 may be configured to generate light having VUV wavelengths. As such, the first measurement subsystem may be configured to perform measurements at VUV wavelengths.

The second measurement subsystem includes light source 246. Light source 246 is configured to direct light to mirror 248. Mirror 248 is configured to direct the light through polarizing component 238 to specimen 232. Light returned from specimen 232 passes through polarizing component 236 to TIR prism 250. TIR prism 250 directs the light to detector 252. TIR prism 250 will not create additional polarization in the light directed to detector 252. Once the light is reflected from TIR prism 250, a polarization insensitive detector may be used to detect the reflected light or a depolarizer may be placed in the optical path of the light between the TIR prism and the detector. TIR prism 250 may be replaced with a mirror. In this manner, additional calibration may be performed to correct the effect of the mirror on the light. Detector 252 may include any suitable detector known in the art such as a spectrometer. In addition, the detector may be selected based on the wavelengths of light at which measurements will be performed by the detector.

Mirror 248 may, in some embodiments, be a folding mirror. Mirrors 248 and TIR prism 250 may be moved out of the optical path during measurements by the first measurement subsystem so as to not interfere with these measurements. Alternatively, mirror 248 and TIR prism 250 may be configured to transmit or reflect light based on wavelength. For example, if the second measurement subsystem is configured to perform measurements at VUV wavelengths, mirror 248 and TIR prism 250 may be configured to reflect VUV light and to transmit light of other wavelengths. In this manner, mirror 248 and TIR prism 250 may function essentially as dichroic beamsplitters.

As with the first measurement subsystem, the second measurement subsystem may be configured as an ellipsometer. As such, polarizing component 238 functions as a polarizer for the ellipsometer, and polarizing component 236 functions as an analyzer for the ellipsometer. In this manner, the second measurement subsystem may be configured as an RAE. In addition, light source 246 may include a spectroscopic or broadband light source. As such, the measurements performed by the second measurement subsystem may include SE or BBSE measurements. Therefore, the second measurement subsystem may be configured as a RASE.

Light source 246 may be configured to generate light having UV wavelengths, DUV wavelengths, visible wavelengths, NIR wavelengths, or a combination thereof. For example, light source 246 may be a Xe lamp. In this manner, the second measurement subsystem may be configured to perform the measurements at UV wavelengths, DUV wavelengths, visible wavelengths, NIR wavelengths, or a combination thereof. Alternatively, light source 246 may be configured to generate light having VUV wavelengths. As such, the second measurement subsystem may be configured to perform measurements at VUV wavelengths.

One particular advantage of the measurement system shown in FIG. 11 is that the measurements of the first and second measurement subsystems can be performed at different wavelengths. In one such embodiment, one of the measurement subsystems may be used for measurements at non-VUV wavelengths while the other measurement subsystem is used for measurements at VUV wavelengths. Therefore, the two measurement subsystems can cover different spectral regions using different light sources. This two beam configuration enables one system to cover a much broader spectrum compared to single beam measurement systems currently being used. In addition, light in different wavelength regimes can be directed along the same optical path, but in different directions. As such, the two beams share the same measurement spot. The two measurement subsystems also share the same calibrations (e.g., $P_0$, $A_a$, angle of incidence (AOI), etc. in ellipsometry applications). Furthermore, although the measurement system includes different measurement subsystems configured to use different light sources and detectors, the measurement subsystems may use a number of common optical components, thereby reducing the cost of the measurement system. The measurement subsystems may also be configured to perform measurements on the specimen at the same time or sequentially one at a time. The measurement system shown in FIG. 11 may be further configured as described herein.

As described above, one of the measurement subsystems can be an RPE, and the other measurement subsystem can be an RAE. Since these two subsystems share the same optics, they measure the exact same spot on the specimen. Therefore, the signals generated by both measurement subsystems can be expressed with the same equation, which is shown below, but the signals are independent of each other.

$$I_{out}=I_{lamp}|r_s|^2(\cos^2 P_2+\sin^2 P_2 \tan^2\Psi)(1+\alpha\cos+\beta\sin 2P_1)$$

where $P_1$ is the angle of the rotating polarizing element, and $P_2$ is the angle of the fixed polarizing element.

As described above, polarizing component 236 acts as a polarizer for the forward propagating beam and as an analyzer for the counter propagating beam. In RAE, the detector sensitivity should be calibrated. A depolarizer can be used to reduce the detector polarization sensitivity. Several calibration methods for correcting detector polarization sensitivity have been developed for RAE, and the method that is used may include any suitable method known in the art.

Figure 12:
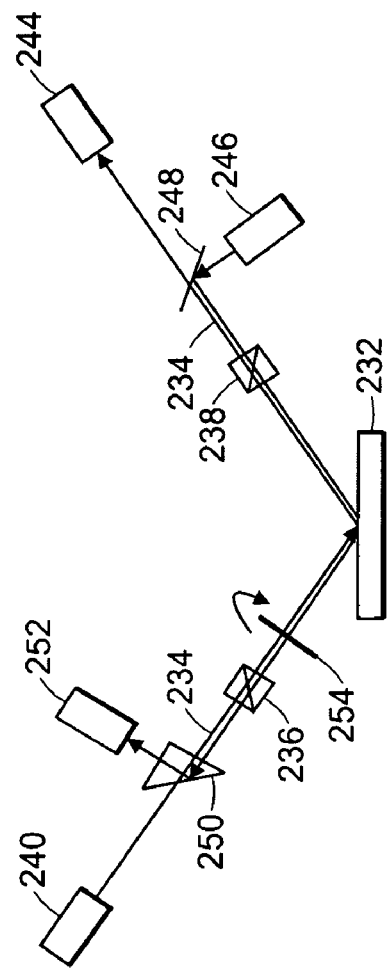
FIGS. 11-12 are schematic diagrams illustrating side views of different embodiments of a measurement system that include two different measurement subsystems that share a common optical path.

FIG. 12 illustrates a different embodiment of the measurement system. Unlike the system shown in FIG. 11, in this embodiment, polarizing component 236 is not configured to rotate. In addition, a position of both polarizing components 236 and 238 may be stationary. This embodiment of the measurement system includes rotating compensator 254 positioned along the common optical path between polarizing component 236 and specimen 232. In this manner, both of the measurement subsystems may use rotating compensator 254 for measurements. As such, the first and second measurement subsystems may be configured as rotating compensator spectroscopic ellipsometers (RCSE). In this case, the two measurement subsystems will have effectively different calibration values such as $A_0$ and $P_0$ values. The measurement system shown in FIG. 12 may be further configured as described herein.

The following description relates to another embodiment of a measurement system that is configured to perform measurements of a specimen. This measurement system includes an optical subsystem that is configured to perform the measurements of the specimen using light in different wavelength regimes that is directed along a common optical path. The different wavelength regimes include VUV, DUV, UV, visible, and NIR wavelength regimes. In some embodiments, the measurement system may be configured as a single SE.

Figure 13:
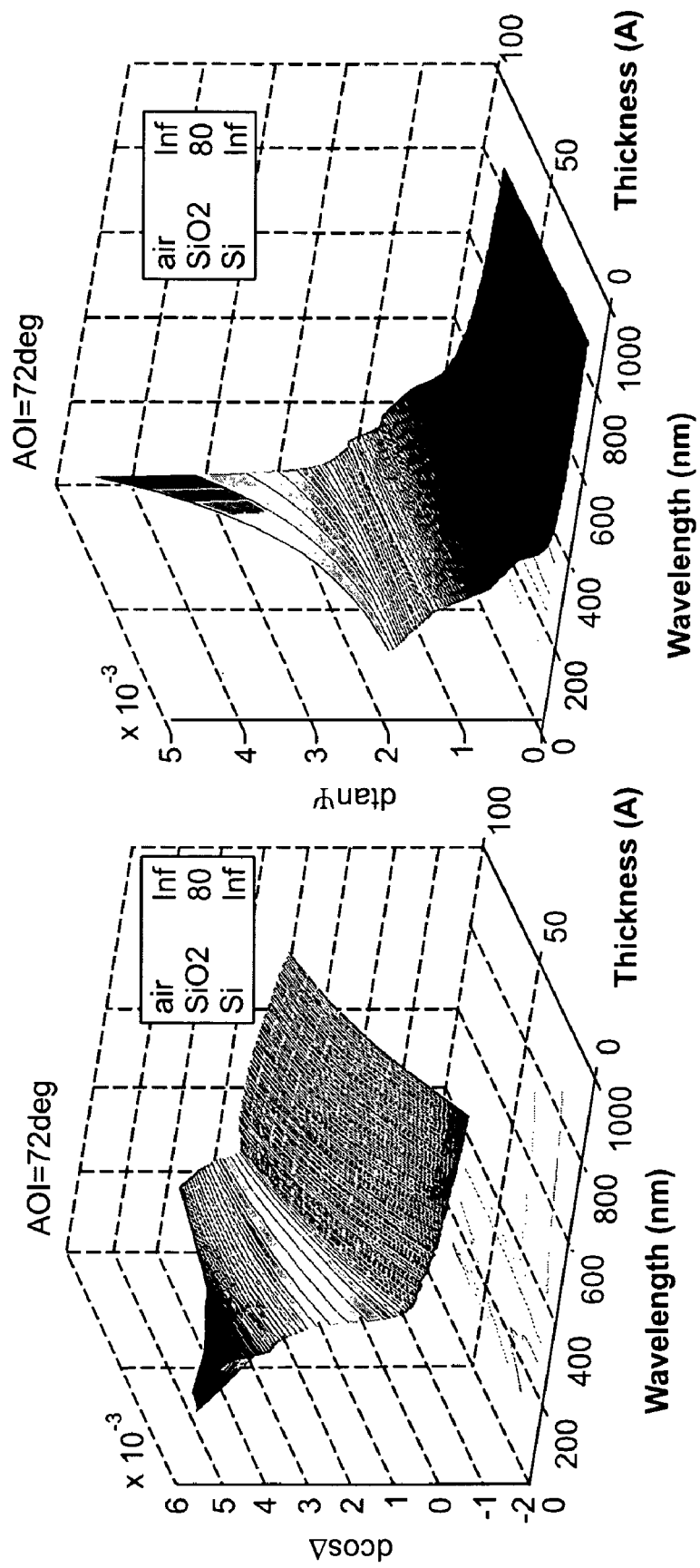
FIG. 13 includes plots illustrating the sensitivity of an ellipsometer to 1 Å thickness changes in a thick oxide layer.

As described above, there is a need for an SE system that covers a wide spectrum of wavelengths from about 150 nm to about 900 nm. For example, the shorter wavelengths in this spectrum provide better performance for determining n, k, and thickness of very thin multilayer film stacks. In addition, as shown in FIG. 13, the ellipsometer sensitivity to 1 Å thickness changes in thick oxide layers is much enhanced at wavelengths below about 300 nm. However, it is also desirable to utilize a wide spectrum of wavelengths for measurements since the large wavelength range reduces the systematic error of the measurements and provides a better measurement of film thickness, especially on thinner films. The systems described below utilize a different broadband design that is capable of meeting the next generation SE requirements at a lower cost.

One currently used SE system has a standard module that covers wavelengths from 200 nm to 900 nm. A 193SE has been introduced to separately address the 190-300 nm spectrum. Recently, a VUVSE using a purge optics only approach has been developed as described in the Patent Application by Fielden et al. that is incorporated by reference above. Thus, a broadband SE system can utilize a combination of two different SE measurement systems. Using a combination of different, separate SE measurement systems to cover a wide spectral range is currently being used in the industry. However, the use of multiple measurement systems represents a significant cost to the overall SE system in terms of hardware and software development efforts. Furthermore, the use of a combination of measurements from different systems to obtain information on the specimen across a wide spectral range makes the calibration and matching difficult between the systems.

Figure 14:
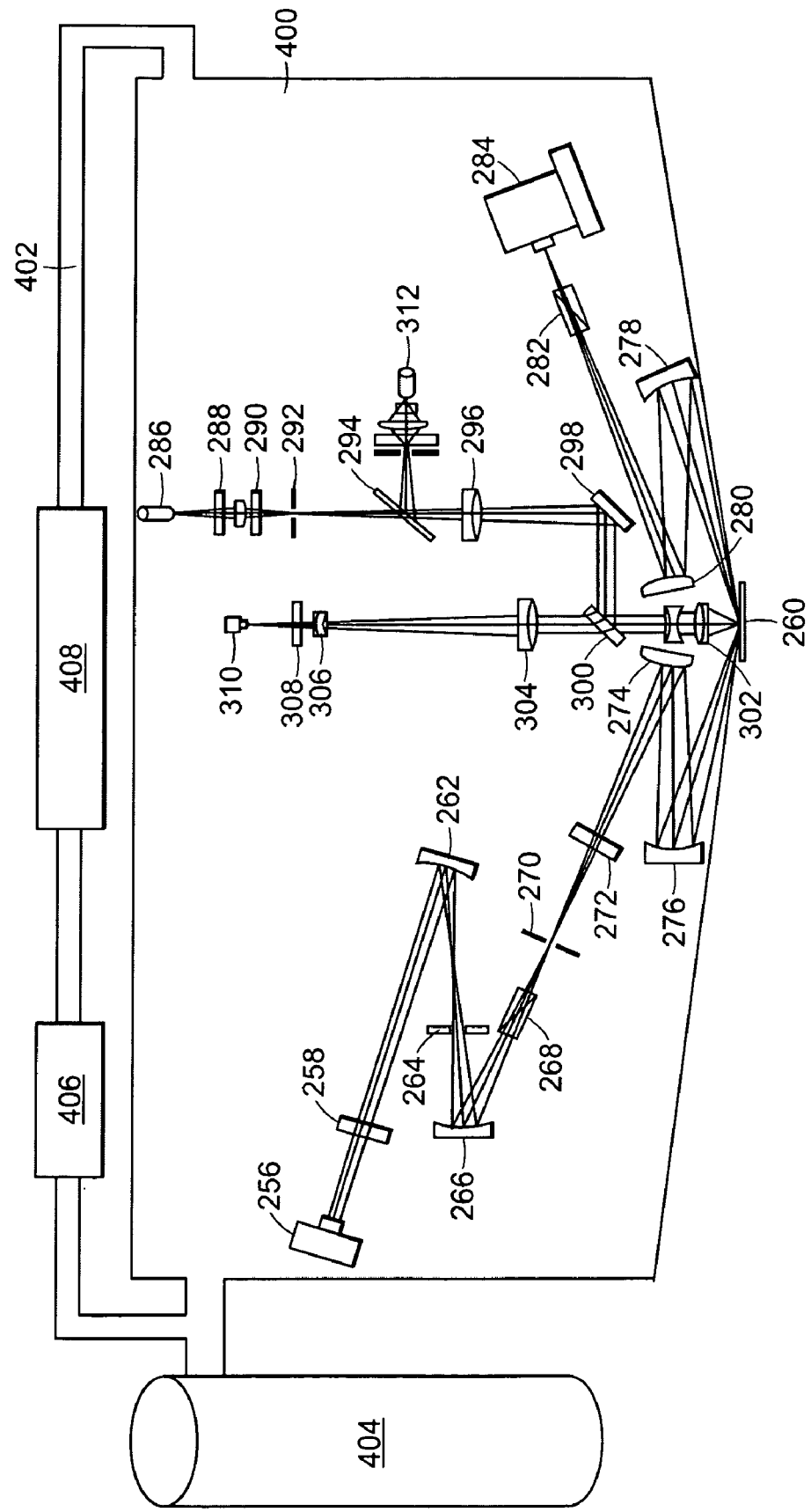
FIG. 14 is a schematic diagram illustrating a side view of an embodiment of a measurement system that includes a VUV purging system.

One embodiment of an optical subsystem that may be included in a measurement system such as a BBSE is shown in FIG. 14. The SE includes light source 256, which may include any of the light sources described herein. Preferably, the light source is a broadband light source. Light from light source 256 is directed to flip-in shutter 258, which if positioned in the optical path, as shown in FIG. 14, prevents light from light source 256 from reaching specimen 260. If flip-in shutter 258 is not positioned in the optical path, light from light source 256 is directed to coupling mirror 262, which directs the light through a pinhole in plate 264 to coupling mirror 266. Coupling mirror 266 directs the light to polarizer 268, which may be configured as described herein. Light exiting polarizer 268 is directed though a slit in plate 270 to apodizer 272. Light from apodizer 272 is directed to focusing mirror 274, which directs the light to focusing mirror 276. Focusing mirror 276 focuses the light on specimen 260 at an oblique angle of incidence.

Light returned from specimen 260 is collected by collection mirror 278, which directs the light to focusing mirror 280. Focusing mirror 280 directs the light to analyzer 282, which may be configured as described herein. Light exiting analyzer 282 is directed to grating spectrometer 284, which may be configured as described herein. The SE system may be configured to function as an RPSE and/or an RASE.

The measurement system may also include a number of additional optical components that form different subsystems of the measurement system. For example, the measurement system may include a pattern recognition subsystem. The pattern recognition subsystem may include optic fiber bundle 286. The optical fiber bundle may be coupled to any appropriate light source known in the art. Light from optical fiber bundle 286 is directed to flip-in neutral density (ND) filter 288 and filter 290. Light exiting filter 290 may be directed through stop 292 and beamsplitter 294 to lens 296. Light from lens 296 is directed onto the specimen by folding mirror 298, beamsplitter 300, and 10× objective lens 302.

Light returned from the specimen is collected by 10× objective 302. Beamsplitter 300 directs a portion of the light collected by the objective to lens 304. Negative lens 306 focuses the light from lens 304 through filter 308 and onto detector 310. Detector 310 may include, for example, a CCD camera. Signals from detector 310 may be used for pattern recognition purposes.

Beamsplitter 300 directs a different portion of the light collected by the objective to folding mirror 298. Light from folding mirror 298 is directed by lens 296 to beamsplitter 294, which directs this portion of the light to detection subsystem 312. Detection subsystem 312 may include, for example, a cross-hair type detection subsystem. Signals generated by detection subsystem 312 may be used for focusing purposes. The optical subsystem shown in FIG. 14 can be further configured as described herein.

The system shown in FIG. 14 preferably has a carefully optimized light source, spectrometer, and purging systems. For example, typically the main light source for VUV applications is a $D_2$ lamp with a $MgF_2$ window. However, the spectra of this lamp diminishes above about 300 nm. A pulsed Xe Lamp is typically used as a light source for a wide spectrum from 140 nm to 1000 nm. However, the large spot size of the Xe lamp, i.e., low brightness, makes it inferior. Furthermore, there are issues with flash lamp noise.

Figure 15:
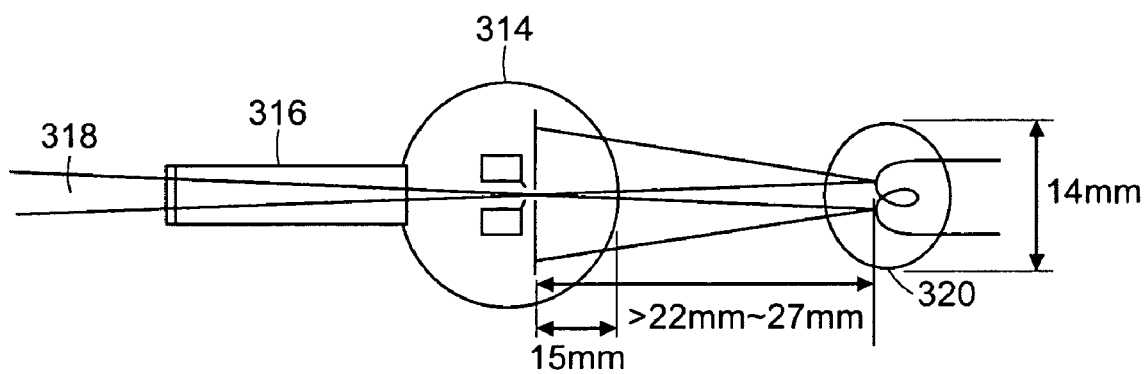
FIG. 15 is a schematic diagram illustrating a side view of one example of a see-thru lamp configuration that may be included in the measurement systems described herein.

A broadband light source can be constructed, however, using a combination of light sources that are configured to direct light along a common optical path. For example, the broadband light source may include a $D_2$ lamp with a see-through window in front of a Xe lamp, one embodiment of which is shown in FIG. 15. In this manner, the optical subsystem may include two or more light sources. Each of the two or more light sources is configured to produce the light for measurements in at least one of the different wavelength regimes. By combining the light sources as described herein, the light in the different wavelength regimes can be directed along a common optical path.

As shown in FIG. 15, $D_2$ lamp 314 includes $MgF_2$ window 316. Light generated by the $D_2$ lamp is projected through the $MgF_2$ window and out of the lamp along optical path 318. The combination light source also includes Xe lamp 320. The $D_2$ lamp is configured as a see-thru lamp in that light generated by the Xe lamp can be projected through $D_2$ lamp 314 and $MgF_2$ window 316 along the same optical path as the light from the $D_2$ lamp.

This combined lamp configuration provides sufficient light across a broadband spectrum in that the Xe lamp intensity is about 68% at 27 mm defocusing. There is, therefore, a 32% loss of photons for the Xe lamp. However, this loss of photons would not compromise the system performance because the Xe lamp is very bright. The limiting photon count of the system will be the $D_2$ lamp. Since the intensity of the VUV light generated by the $D_2$ lamp will be substantially lower that the intensity of the UV-NIR light generated by the Xe lamp, an ND filter may be used to lower the intensity of the light generated by the Xe lamp when both lamps are being used simultaneously. In addition, the combined lamp has relatively low lamp noise. Furthermore, a broadband light source that includes a combination of two lamps as shown in FIG. 15 can be used for SE applications since this light source configuration does not introduce partial polarization effects to the light. In an alternative embodiment, the light from two or more light sources may be combined as described above (e.g., using one or more TIR prisms).

It is also a real challenge to make a broadband spectrometer that can be used for measurements from 150 nm to 900 nm. The conventional approach for a wideband spectrometer is to use a prism, a grating with order blocking filters, and an Echelle grating with cross dispersive elements.

Figure 16:
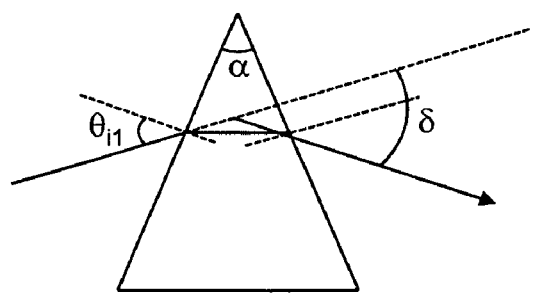
FIG. 16 is a schematic diagram illustrating the deflection angle of a prism that may be included in a prism spectrometer.
Figure 17:
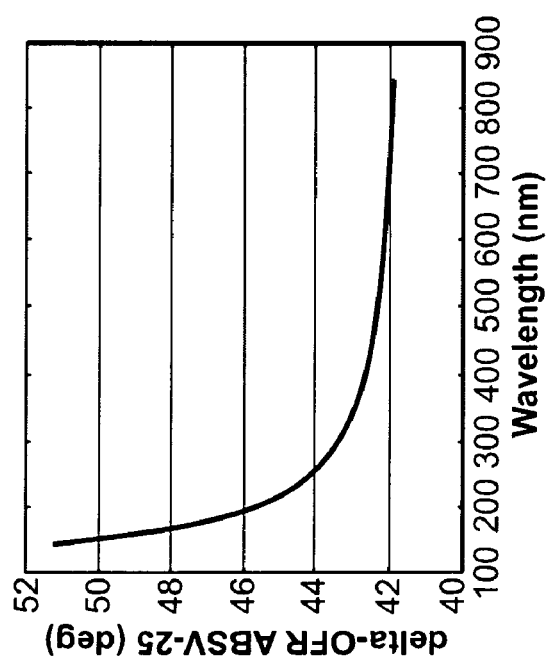
FIG. 17 is a plot illustrating prism deflection angle as a function of wavelength for a typical prism.

The prism spectrometer has been used in older generation SEs. The best candidate for the dispersive material of the prism is $CaF_2$, which is transparent at VUV with no birefringent effects. The deflection angle of the prism can be expressed mathematically and graphically as shown in FIG. 16. The prism deflection angles are shown in FIG. 17 as a function of wavelength for a typical prism. In particular, the prism deflection angles are shown for a dispersing prism fabricated of $CaF_2$ for the VUV regime (e.g., 130 nm to 250 nm) that is commercially available from OFR, Inc. (Optics for Research), Verona, N.J., as Catalog Number ABSV-15. The prism has an apex angle, α, of 69.9°, and a Brewster's angle of 57°. As shown in FIG. 17, the dispersion of the prism is relatively small for wavelengths greater than 300 nm. Therefore, using such prisms as the primary dispersive elements can lead to under sampling at longer wavelengths, which is why grating based spectrometers are often used at these wavelengths. Furthermore, it is difficult to calibrate the spectrometer due to such nonlinearity in the dispersion angle.

Figure 18:
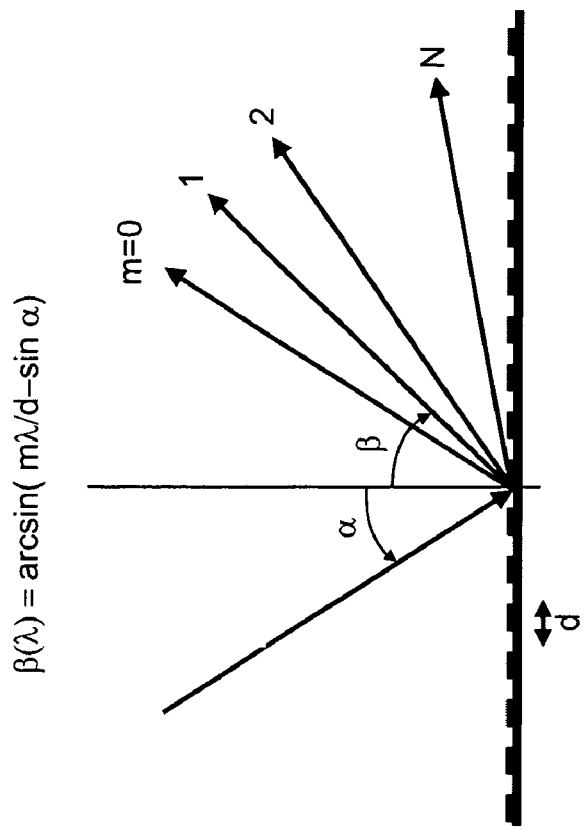
FIG. 18 is a schematic diagram illustrating the diffraction orders that are produced by a grating of a grating based wideband spectrometer.
Figure 19:
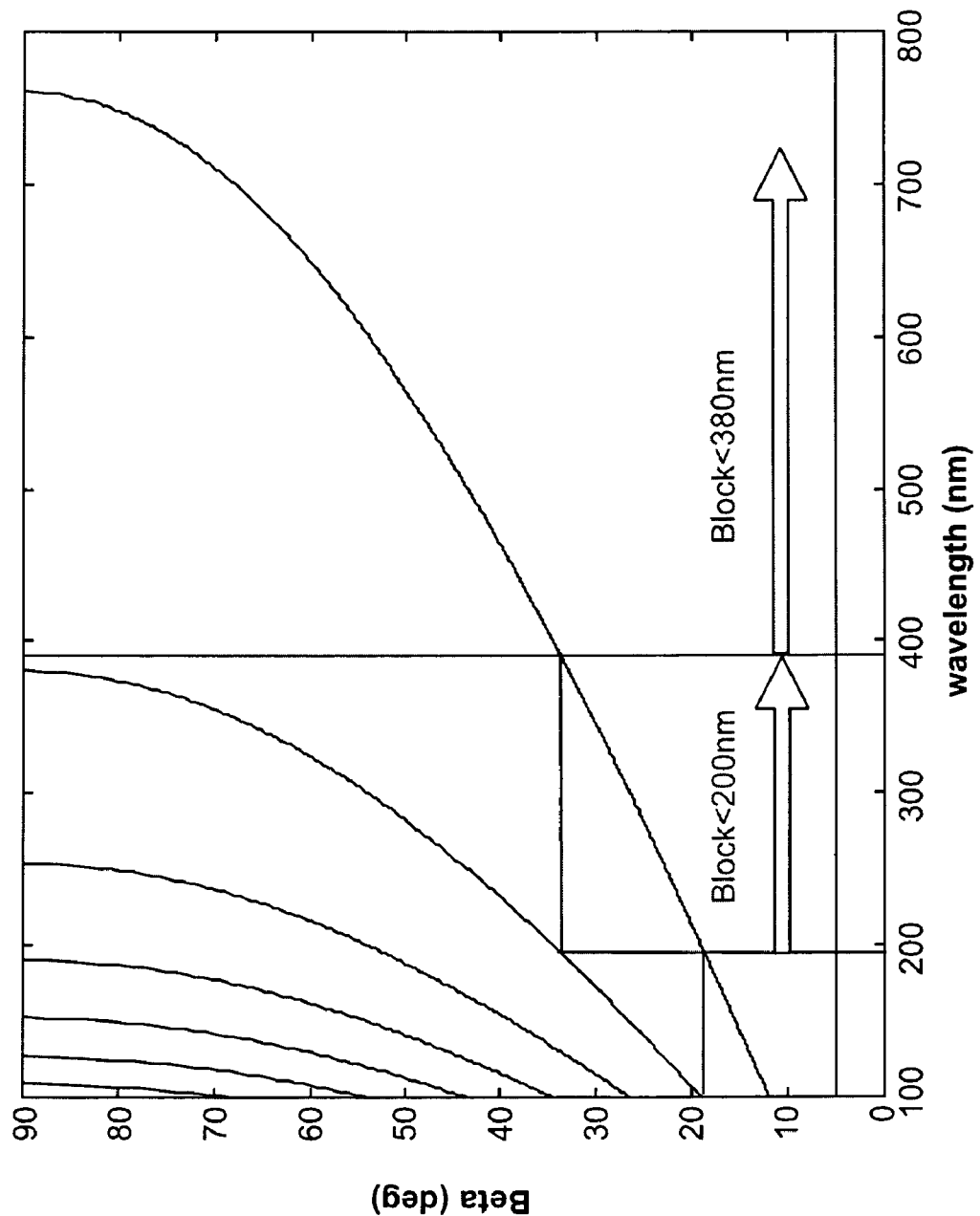
FIG. 19 is a plot illustrating how an order blocking filter is designed.
Figure 20:
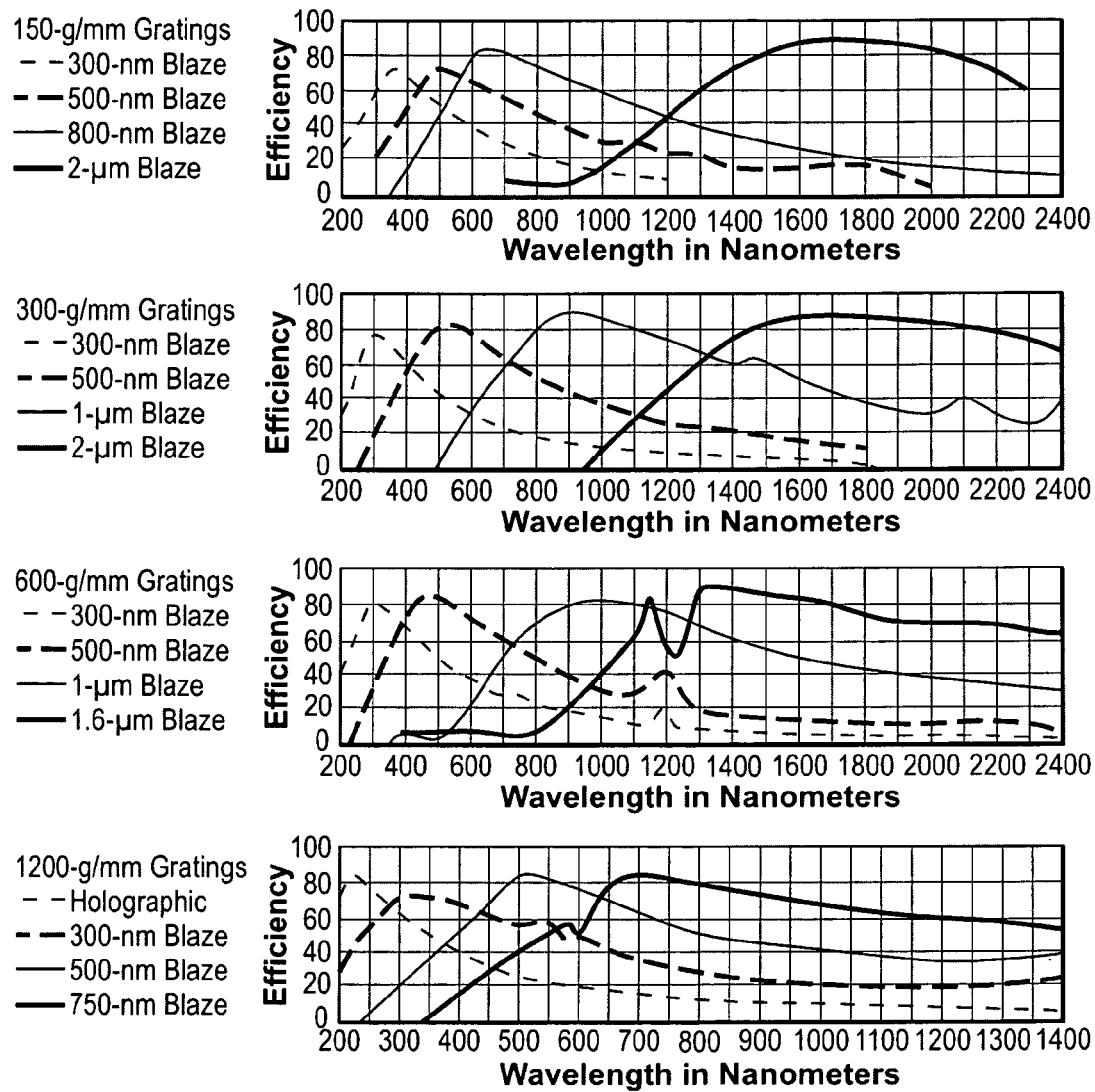
FIG. 20 includes plots that illustrate the efficiency of a typical grating as a function of wavelength.

A grating based wideband spectrometer such as the one used in the F5x system, commercially available from KLA-Tencor, Inc., San Jose, Calif., compromises on grating efficiency and order overlapping. The grating gives a much more linear dispersion that that of prisms. However, the grating also produces multiple diffraction orders so that one cannot resolve all wavelengths uniquely as shown in FIGS. 18 and 19. The data shown in FIG. 19 is for a grating having 1200 G/mm and an apex angle of 5 degrees. Furthermore, the efficiency of a grating usually peaks at a certain wavelength, as shown in FIG. 20, which illustrates the grating efficiency as a function of wavelength for a number of different gratings. High efficiency over the whole range is not possible with this approach, as shown in FIG. 21, which illustrates data for optimal working wavelength ranges for the most commonly requested gratings from Roper Scientific, Acton Research, Acton, Mass. One common approach to this problem is to use a grating turret which reduces throughput to an unacceptable level. Extending the wide grating efficiency over a wide range posted an even more serious challenge in terms of order overlapping and grating efficiency.

To cover a wide spectrum, an Echelle spectrometer can be used that covers UV to NIR with high resolution (Mount and Fastie, 1978; Wang et al., 2000?). Such spectrometers have been used by astronomers for many years. The Echelle grating has a period that is much less than the wavelength being measured so there will be many (from a few tens to 200) diffraction orders. A prism or a grating is used as the cross disperser to spread out the different grating orders. There are two key advantages with this approach. First, the shorter wavelengths can be resolved by higher order diffraction such that the resolving power ($\Delta\lambda/\lambda$) of the spectrometer can be maintained fairly uniformly. Secondly, the efficiencies of the higher order diffraction also shifts to shorter wavelengths. Therefore, one can obtain fairly uniform efficiency over the entire wavelength range. However, drawbacks of this approach are mainly lower SNR, high cost, and low throughput. Prism cross dispersers are most often used for their high efficiency in comparison to gratings. A prism cross disperser separation gets smaller at longer wavelengths, as shown in FIG. 17.

Figure 22:
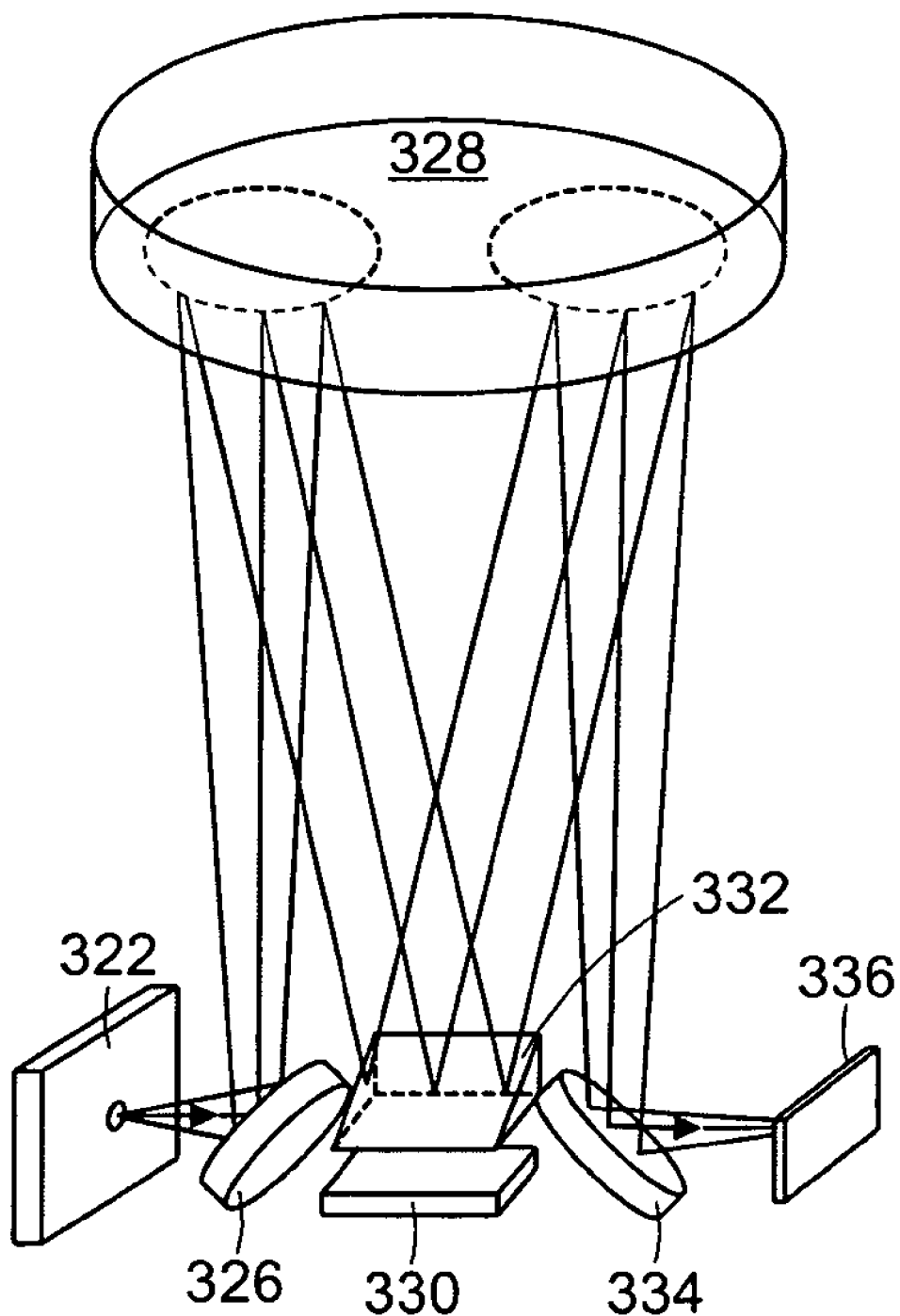
FIG. 22 is a schematic diagram illustrating a perspective view of an echelle spectrometer that is currently used.

A perspective drawing of an Echelle spectrometer (SE200) that is commercially available from Catalina Scientific, Tucson, Ariz., is shown in FIG. 22. The spectrometer includes entrance aperture 322. Light entering the spectrometer through the entrance aperture is directed by mirror 326 to primary mirror 328. Primary mirror 328 directs light to echelle grating 330, which diffracts the light at angles that vary with wavelength. Light diffracted by the grating is directed to prism 332, which disperses different orders of the diffracted light to produce a two-dimensional diffraction pattern. The light exiting the prism is directed back to primary mirror 328, which directs the light to mirror 334. Mirror 334 directs the light to CCD 336.

Figure 23:
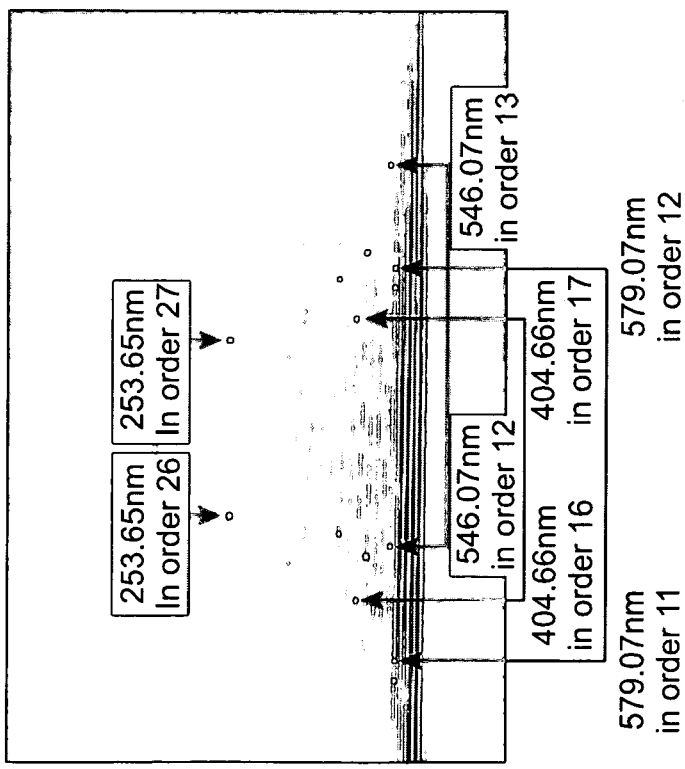
FIG. 23 is a plot illustrating that the spacing between orders is much smaller for longer wavelengths than for shorter wavelengths.

FIG. 23 illustrates a spectrograph of light from an Hg lamp superimposed over light from a $D_2$ lamp and a tungsten lamp on a CCD camera. The spacing between the orders is much smaller for higher wavelengths, as shown in FIG. 23. To keep a high SNR, the entrance slit of the spectrometer has to be substantially small, which reduces the amount of incoming light. As such, there is a delicate balance between order cross talk and photon counts.

Another design to reduce the order cross talk uses multiple refractive prismatic cross dispersers to compensate for the coma and stigmatism and to flatten the image field as described in U.S. Pat. No. 5,859,702 to Lindblom, which is incorporated by reference as if fully set forth herein. However, such a design does not extend down to the VUV region due to lack of suitable materials for the compensating prisms. Furthermore, the complicated optical arrangement make alignment and calibration difficult. In addition, this design did not increase the order distance at longer wavelength. Another fundamental limitation for Echelle spectrometers is the use of a CCD camera to record all of the different orders. For example, it is very expensive (on the order of tens of thousands of dollars) to use a high speed and low noise CCD camera. Therefore, Echelle spectrometers are at least ten times more expensive than conventional spectrometers. In addition, the signal conditioning and order sorting adds substantial processing time to the system and limits the throughput.

Figure 24:
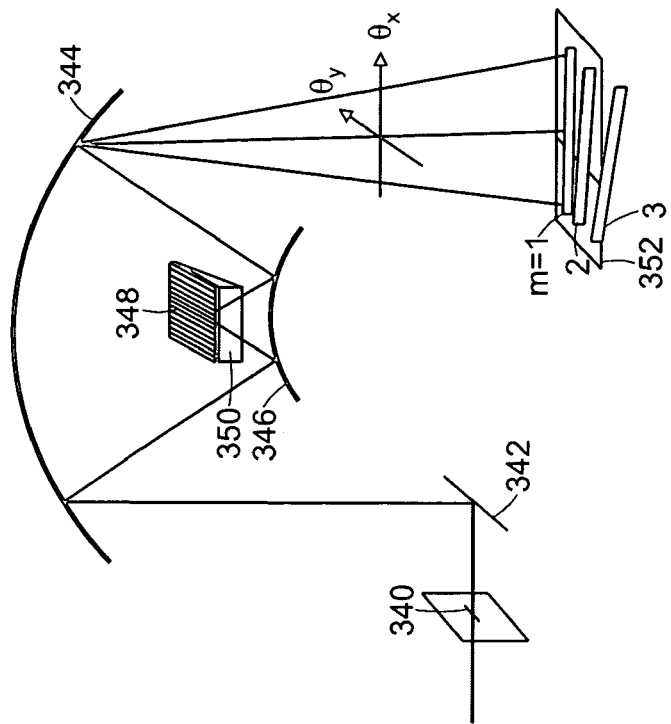
FIG. 24 is a schematic diagram illustrating a perspective view of an embodiment of a spectrometer that can be included in the measurement system embodiments described herein.

A modified version of an Echelle spectrometer is proposed herein to cover VUV to NIR. This Echelle spectrometer improves the spectral resolution and resolving power of the conventional spectrometers and maintains their high SNR, low cost, and throughput. This embodiment of the Echelle broadband spectrometer employs a combination of a prism cross dispersion element and one or more order blocking filters. For example, as shown in FIG. 24, the Echelle spectrometer includes entrance slit 340. Light entering the spectrometer through the entrance slit is directed to mirror 342. Mirror 342 directs the light to mirror 344, which directs the light to mirror 346. Mirror 346 directs the light to plane grating 348, which diffracts the light at angles that vary with wavelength. Light diffracted by plane grating 348 is directed to prism 350. Prism 350 disperses different orders of the diffracted light to get a two-dimensional diffraction pattern of light, which is directed by mirror 346 to mirror 344. Mirror 344 directs the two-dimensional diffraction pattern of light to order blocking filter 352. Light that passes through the order blocking filter is directed to a detection element (not shown) such as a CCD camera or any other suitable detection element known in the art.

Figures 25, 26:
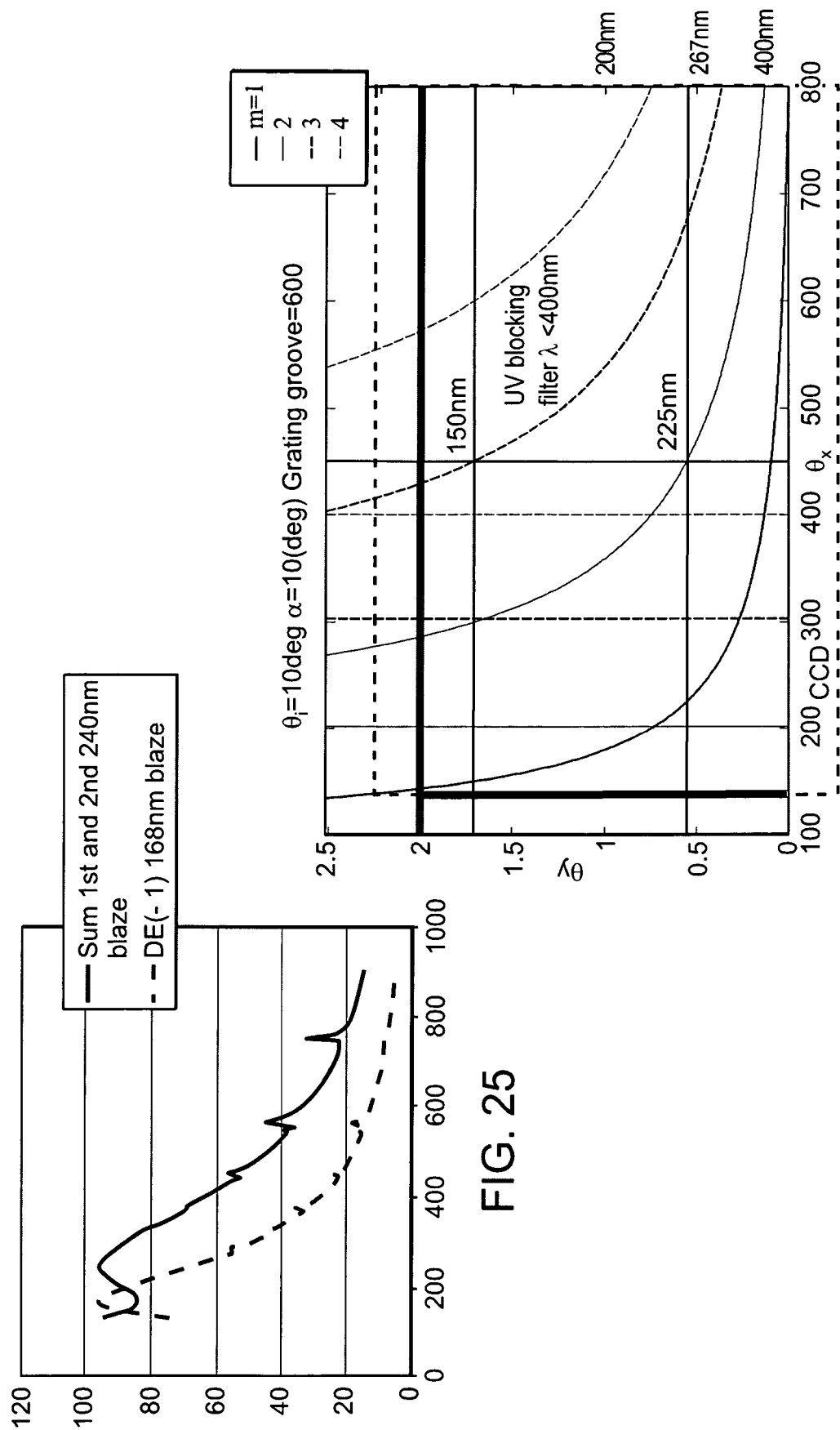
FIG. 25 is a plot illustrating the efficiency of different gratings when more than one grating order is used.
FIG. 26 is a plot illustrating blocking of short wavelengths at the long wavelength range using an order blocking filter.

In some embodiments, the one or more order blocking filters are configured to allow two or more grating orders to impinge on the detection element. Each of the two or more grating orders are used for measurements in different wavelength ranges across the different wavelength regimes. With the use of two or more grating orders, the overall diffraction efficiency can be maintained over the whole range of interest. For example, using a 600 g/mm grating, blazed at 400 nm, it is estimated that the first order can cover 200 nm to 800 nm, as shown in FIG. 26, which illustrates dispersion in wavelength with α=10 degrees. The estimated spectral resolution is about 0.5 nm. The second order can cover 140 nm to 400 nm with double the spectral resolution. The diffraction efficiency is substantially improved using both the first and the second grating orders as compared to just one grating as shown in FIG. 25, which illustrates the grating efficiencies of holographic gratings blazed at 240 nm and 168 nm. A higher efficiency improves the signal and reduces photon scattering. Furthermore, a holographic grating has substantially reduced scattering and ghosts. However, it is generally difficult to make blaze angles small for very short wavelengths. The current approach thus can improve on the collection efficiency and scattering.

A $CaF_2$ prism is used as the cross dispersive element (e.g., prism 350) to separate the orders and a UV blocking filter is used to keep the separation of the different orders large to enhance the SNR. The spectrometer can be a modified version of the F5x spectrometer. For a typical spectrometer, the useful diffraction angles are about 20 degrees. Linear CCD arrays are typically 128 pixels×1024 pixels. Using the same lens for collimating, the maximum dispersion angle is about 3 degrees. A spectrometer normally uses a rectangle to collect more photons to increase throughput without degrading spectra. However, it requires the order overlap to be smaller than the CCD background noise. The orders will overlap especially at longer wavelengths due to the small dispersion of the prism. The order-blocking filter can block all of the short wavelengths during measurements in the long wavelength range, as shown in FIG. 26, thereby maintaining the order separation and the SNR. The order blocking filter did not have to be sharp in order to block the short wavelengths. For example, all wavelengths below 225 inn at about 450 nm can be blocked with the order blocking filter.

An added benefit of using an order blocking filter in the modified Echelle spectrometer is improved readout speed. For example, all of the relevant spectral information can be binned twice in comparison to the conventional Echelle spectrometer which needs to be binned 128 times in this case. Therefore, a broadband spectrometer is provided without increasing cost, speed, and signal quality.

An enhancement in signal quality of the SE system can be obtained using a circulating $N_2$ purification system, as shown in FIG. 14. As shown in FIG. 14, the measurement system may include measurement chamber 400 in which the optical subsystem is disposed. Measurement chamber 400 is coupled to recycle loop 402. Recycle loop 402 is coupled to purge gas source 404. The purge gas may include $N_2$ or any other appropriate purge gas known in the art. Recycle loop 402 also includes pump 406, which is configured to move the purge gas from the purge gas source or the measurement chamber through purge gas purifier 408 and back into the measurement chamber. The purge gas purifier may include any appropriate purifier known in the art such as commercially available point-of-use purifiers based on gettering techniques.

Recycle loop 402 is configured to purify a purge gas from purge gas source 404 or the measurement chamber and to supply the purified purge gas to measurement chamber 400. The purification system may include a number of other components such as valves, pressure gauges, flow meters, or any other suitable components known in the art. This embodiment of the purification system can be used to obtain relatively low vapor and $O_2$ content in the purge area (i.e., the area inside measurement chamber 400) without increasing turbulence at the opening near specimen 260 and without dumping a large quantity of purge gas into the fab. In this manner, one embodiment of a measurement system may include a combination of an improved broadband light source, an improved broadband spectrometer, and an improved purification subsystem with an opening for measurements.

As described above, a cross dispersion spectrometer is provided that can cover spectral ranges from VUV to NIR. There are a number of concerns with broadband grating based spectrometers such as light scattering and throughput, dynamic range of the detector, and resolution. In particular, in ellipsometry applications, the light scattering from a grating can cause erroneous measurements. The light scattering in the VUV-UV range generally has a relatively large background signal due to the relatively low intensity in this range. In addition, the VUV-UV light throughput is low due to the large number of reflections in the grating spectrometers. As a result, these grating based systems are shot-noise limited. In addition, the non-uniform light intensity across the spectrum also reduces the accuracy of the measurement. For example, the best candidate detector is a back-thinned CCD, which has high efficiency throughout the spectrum. However, it has a relatively low dynamic range. Therefore, the large variation in spectral intensity results in substantially low photon numbers at VUV-UV. As a result, the measurement SNR becomes low in the VUV-UV regime due to shot noise and digitize noise. However, a broadband spectrometer preferably has spectral resolution in these wavelength regimes for measuring thick films.

One way to achieve this spectral resolution in the VUV-UV regimes is to use a high or low pass filter that separates the spectrum above and below around 300 nm. The dynamic range, light scattering, and resolution issues described above can be addressed in this manner. However, such a filter does not exist mainly due to the lack of transparent coating materials at VUV.

Figure 27:
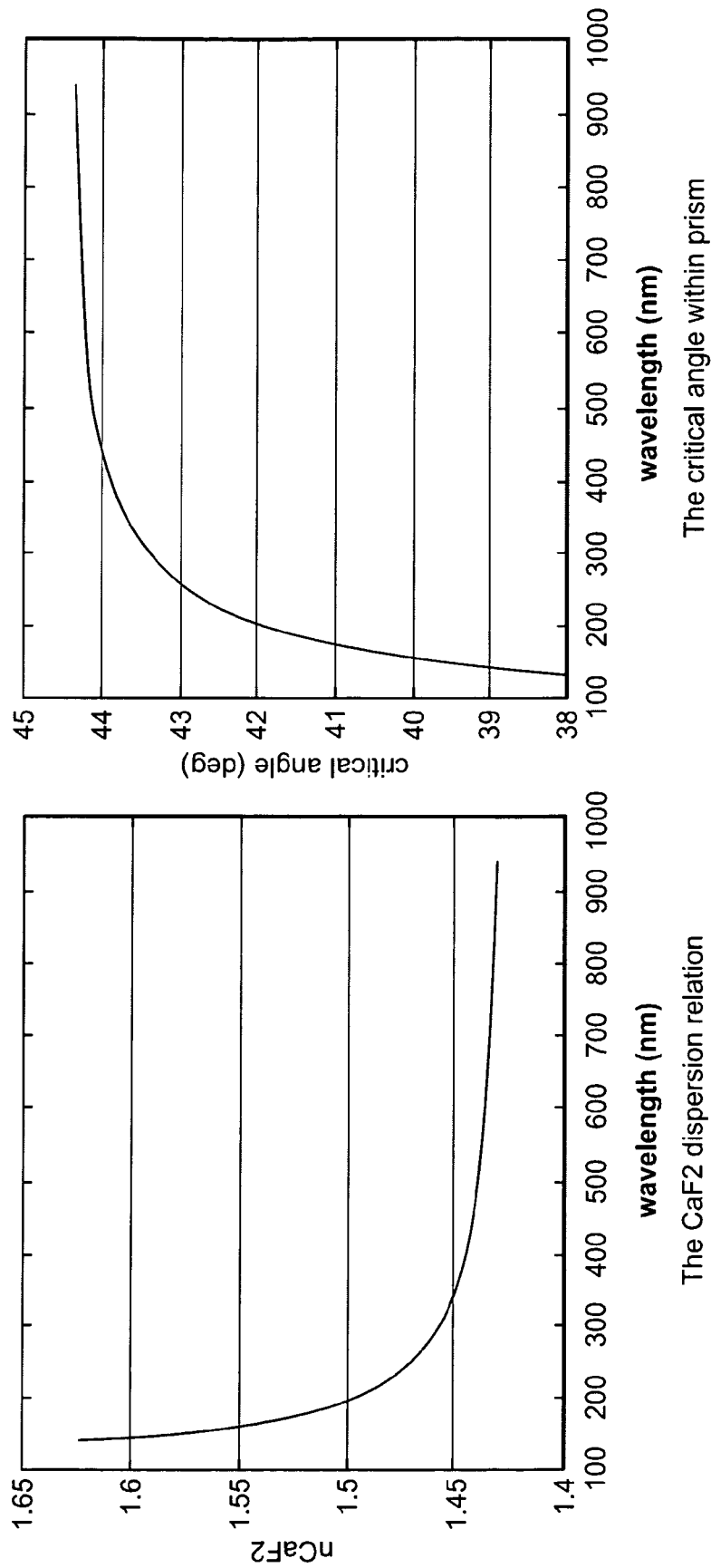
FIG. 27 includes plots illustrating refractive index and critical angle of a prism as a function of wavelength.

In some embodiments, the optical subsystem may include a TIR prism configured to direct at least two of the different wavelength regimes to different detection elements. In this manner, the spectrum can be separated efficiently based on the TIR effect, which is described further herein. When light strikes an optical surface at an angle higher than its critical angle, it will be reflected without any loss in intensity. In most materials, the refractive index is higher in UV than visible. It increases rapidly at wavelengths below about 300 nm. FIG. 27 illustrates refractive index and the critical angle as a function of the wavelength for a $CaF_2$ prism. As shown in FIG. 27, the critical angle increases with wavelength. When light with a plurality of wavelengths strikes the prism surface around the critical angle of a particular wavelength, say 300 nm, then all wavelengths lower than 300 nm will be reflected by the $CaF_2$ prism while significant portions of the wavelengths longer than 300 nm will be transmitted.

Figure 28:
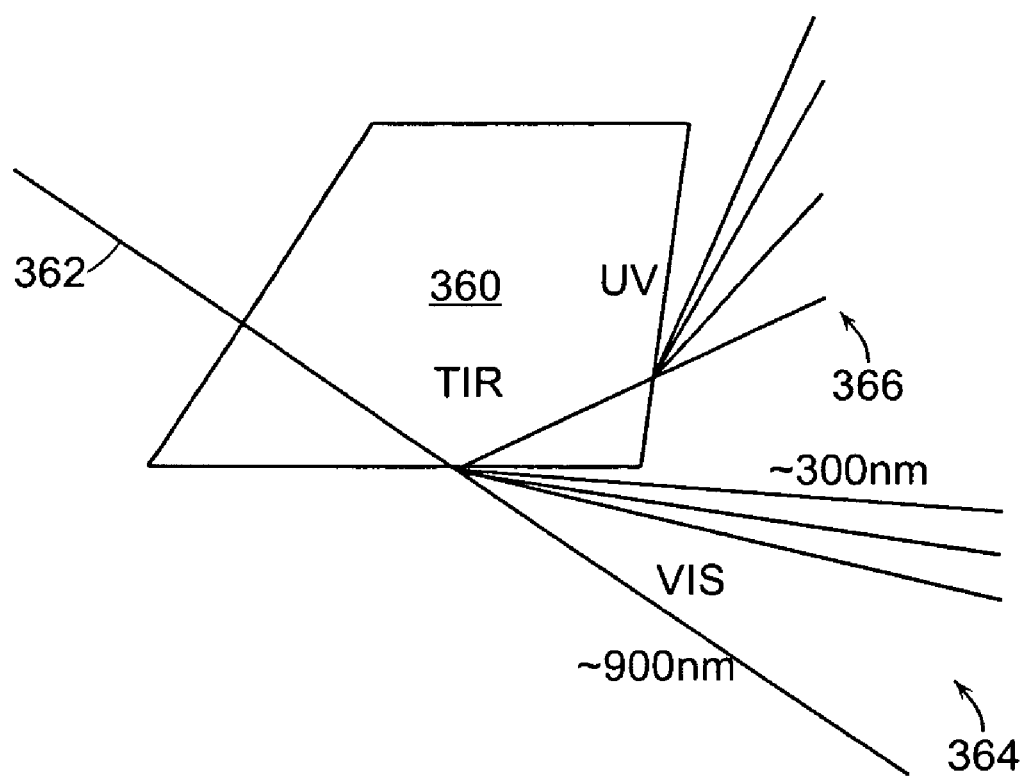
FIG. 28 is a schematic diagram illustrating the dispersion of wavelength on two prism surfaces.

In one embodiment, the broadband spectrometer utilizes the dispersion of wavelengths on two prism surfaces, as shown in FIG. 28. In particular, TIR prism 360 can be used to separate light in the visible and VUV regimes. Light 362 from a collection subsystem (not shown) enters TIR prism 360. The light enters perpendicularly into the first prism surface. As this light hits the second surface of the TIR prism at an angle around the 300 nm critical angle, light with wavelengths longer than around 300 nm will exit the prism via the second surface. The incident angle of this surface is less than the critical angle. In this manner, portion 364 of the light exits one side of the TIR prism, which includes light having wavelengths from about 300 nm to about 900 nm. This portion of the light can be directed to a spectrometer that is configured to detect light having these wavelengths. Light of all wavelengths exiting the third prism surface also experience wavelength dispersion. In this manner, portion 366 of the light exits a different side of the TIR prism and includes light in the UV and VUV regimes. This portion of the light can be directed to a different spectrometer that is configured to detect light in these wavelength regimes. In this manner, one embodiment of a broadband spectrometer includes a novel TIR wavelength separator that can act as a hot/cold mirror for any cut-off wavelength from VUV to NIR. In addition, the broadband spectrometer can include separately optimized detection subsystems for both the VUV-UV and VIS-NIR regions. Therefore, in one embodiment, a broadband spectrometer may include a single TIR prism.

Figure 29:
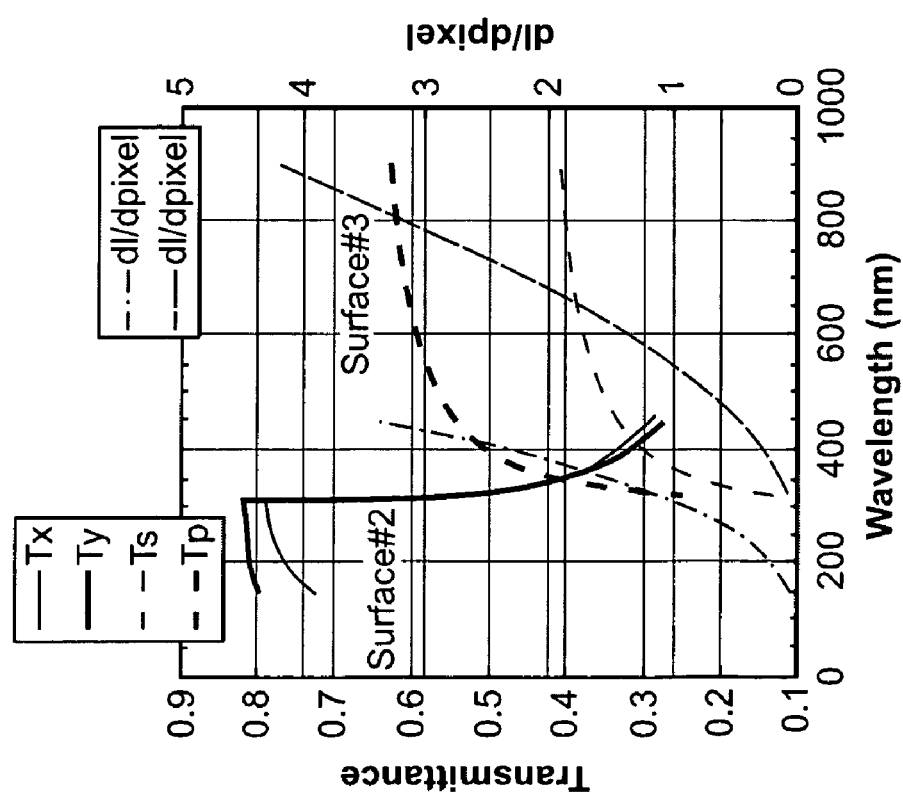
FIG. 29 is a plot illustrating throughput efficiency of a prism as a function of wavelength.

FIG. 29 shows the throughput efficiency vs. wavelength for the TIR prism. The prism facet angle can be optimized to adjust the cut-off wavelength and dispersion. By using appropriate optics, the angular dispersed wavelengths can be focused to a CCD or linear detector array to form a broadband spectrometer. Since $CaF_2$ material is transparent from VUV to IR, very high throughput can be obtained.

Figure 30:
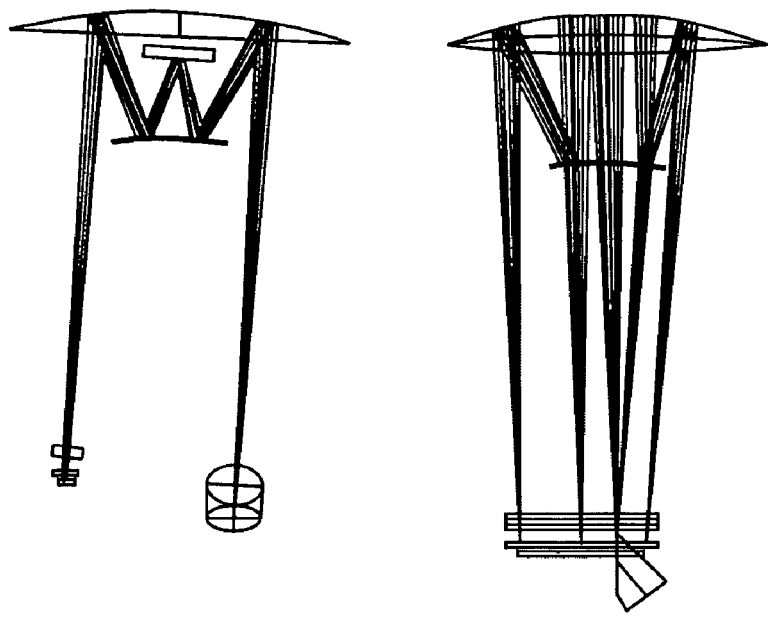
FIG. 30 is a schematic diagram illustrating the collimation and reflection of the visible-near infrared portion of a spectra from a grating, which provides wavelength dispersion that is perpendicular to the third prism surface dispersion plane.

It is desirable to have high wavelength resolution at NIR for thick film measurements. The wavelength dispersion decreases at longer wavelengths in prism spectrometers. One way to increase the dispersion is to use a prism grating combination as the spectrometer. The VIS-NIR portion of the spectra will be collimated and reflected from a grating to provide wavelength dispersion perpendicular to the third prism surface dispersion plane, as shown in FIG. 30. The grating will provide a linear dispersion for the visible to NIR wavelength range. The shorter wavelength range and the linear dispersion will give a higher wavelength resolution at NIR. One drawback of this approach is the use of the grating and the extra collimating mirrors. These components reduce the throughput for VIS to NIR. However, there are plenty of photons at these wavelength ranges so one can trade photon count with resolution and linearity with light throughput.

The systems described above, therefore, are configured as single BBSE measurement systems in which light in wavelengths from VUV to NIR goes through a common optical path. Such an SE improves precision and matching and extends accurate measurement down to the VUV region. In addition, the system is designed to have high signal quality, fast measurement, and low cost.

Further modifications and alternative embodiments of various aspects of the invention may be apparent to those skilled in the art in view of this description. For example, measurement systems configured to perform measurements of a specimen and illumination subsystems configured to provide illumination for a measurement system are provided. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A measurement system configured to perform measurements of a specimen, comprising:
   a first measurement subsystem configured to perform measurements of the specimen by directing light in a first direction along an optical path from a first polarizing component to a second polarizing component; and
   a second measurement subsystem configured to perform measurements of the specimen by directing light in a second direction along the optical path from the second polarizing component to the first polarizing component, wherein the second direction is opposite to the first direction, and wherein the first and second polarizing components are used by the first and second measurement subsystems for the measurements.

2. The measurement system of claim 1, wherein the measurements of the first and second measurement subsystems comprise spectroscopic ellipsometry measurements.

3. The measurement system of claim 1, wherein the measurements of the first and second measurement subsystems are performed at different wavelengths.

4. The measurement system of claim 1, wherein the first measurement subsystem is further configured to perform the measurements at ultraviolet wavelengths, visible wavelengths, near infrared wavelengths, or a combination thereof.

5. The measurement system of claim 1, wherein the second measurement subsystem is further configured to perform the measurements at vacuum ultraviolet wavelengths.

6. The measurement system of claim 1, wherein the first measurement subsystem is further configured as a rotating polarizer spectroscopic ellipsometer, and wherein the second measurement subsystem is further configured as a rotating analyzer spectroscopic ellipsometer.

7. The measurement system of claim 1, wherein the first and second measurement subsystems are further configured as rotating compensator spectroscopic ellipsometers.

* * * * *